US011255855B1

(12) United States Patent
Huang et al.

(10) Patent No.: US 11,255,855 B1
(45) Date of Patent: *Feb. 22, 2022

(54) COVID-19 SPIKE-ACE2 BINDING ASSAY FOR DRUG AND ANTIBODY SCREENING

(71) Applicant: RayBiotech Life, Inc., Peachtree Corners, GA (US)

(72) Inventors: Ruo-Pan Huang, Johns Creek, GA (US); Hao Tang, Duluth, GA (US); Shuhong Luo, Duluth, GA (US); Jianmin Fang, Athens, GA (US)

(73) Assignee: RayBiotech Life, Inc., Peachtree Corners, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/411,390

(22) Filed: Aug. 25, 2021

Related U.S. Application Data

(62) Division of application No. 17/141,837, filed on Jan. 5, 2021, now Pat. No. 11,105,804.

(60) Provisional application No. 63/125,087, filed on Dec. 14, 2020.

(51) Int. Cl.
*G01N 33/569* (2006.01)
*G01N 25/20* (2006.01)

(52) U.S. Cl.
CPC . *G01N 33/56983* (2013.01); *G01N 2333/165* (2013.01); *G01N 2333/948* (2013.01); *G01N 2500/02* (2013.01); *G01N 2500/20* (2013.01)

(58) Field of Classification Search
CPC .............. A61K 35/761; A61K 2300/00; A61K 38/177; A61K 31/704; A61K 2039/505; A61P 35/04; C12N 15/86; C12N 2710/10343; C12N 2710/10032; C07K 14/165; C07K 2317/33; G01N 2333/705; G01N 2510/00
See application file for complete search history.

(56) References Cited

PUBLICATIONS

Aubin Moutal et al., "SARS-CoV-2 spike protein co-opts VEGF-A/neuropilin-1 receptor signaling to induce analgesia", Pain. Jan. 2021;162(1):243-252. doi: 10.1097/j.pain.0000000000002097. PMID: 33009246; PMCID: PMC7737878.
U.S. Appl. No. 17/141,837, filed Jan. 5, 2021.
U.S. Appl. No. 17/197,216, filed Mar. 10, 2021.
RayBio® COVID-19 S-Protein (S1RBD) ELISA Kit Protocol, www.RayBiotech.com/ELISA-Kits, Catalog #: ELV-COVID19S1, User Manual Last revised Jun. 14, 2021.
RayBio® COVID-19 Spike-AXL Binding Assay Kit I, For screening COVID-19 drugs and antibodies targeting the Spike-AXL protein interaction, catalog Nos. CoV-AXLS1-1 (1 plate kit) CoV-AXLS1-2 (2 plate kit) CoV-AXLS1-5 (5 plate kit). User Manual Last revised: Apr. 27, 2021, www.RayBiotech.com.
RayBio® Custom ELISA Kit, Catalog #: EL-PRELIM, User Manual Last revised Feb. 6, 2020, www.RayBiotech.com.
RayBio® Human ACE-2 ELISA Kit, Catalog #: ELH-ACE2, User Manual Last revised Jun. 14, 2021, www.Ray Biotech.com.
U.S. Appl. No. 17/348,153, filed Jun. 15, 2021.

*Primary Examiner* — Bao Q Li
(74) *Attorney, Agent, or Firm* — Thomas | Horstemeyer, LLP

(57) ABSTRACT

The present disclosure an ELISA-based assay that uses a glycosylated polypeptide fragment derived from the SARS-CoV-2 spike protein (Covid-19) receptor binding domain (S1RBD) that has affinity for the extracellular domain of Angiotensin Converting Enzyme 2 (ACE2). The S1RBD polypeptide is generated by expression of an encoding nucleic acid by a human cell expression system resulting in glycosylation of the expressed spike receptor binding domain (S1RBD) protein at least at the N343 N-glycosylation site thereof, and which surprisingly and significantly increases the affinity of the S1RBD for ACE2, provides a significant increase in the sensitivity of the assay compared to other known assays.

3 Claims, 17 Drawing Sheets

Specification includes a Sequence Listing.

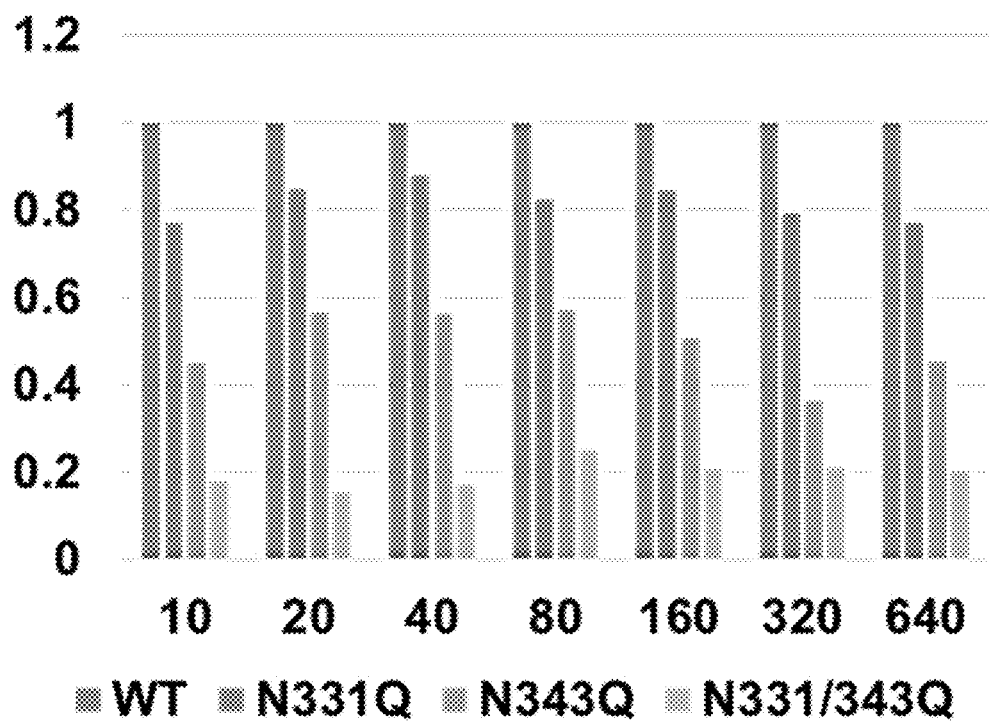
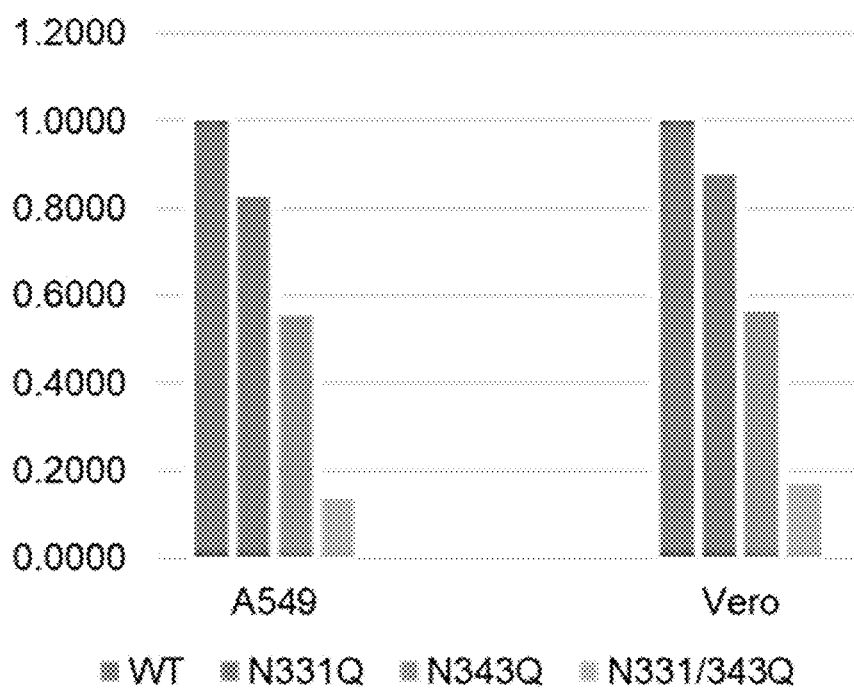
1:40 dilution
*Fig. 9*

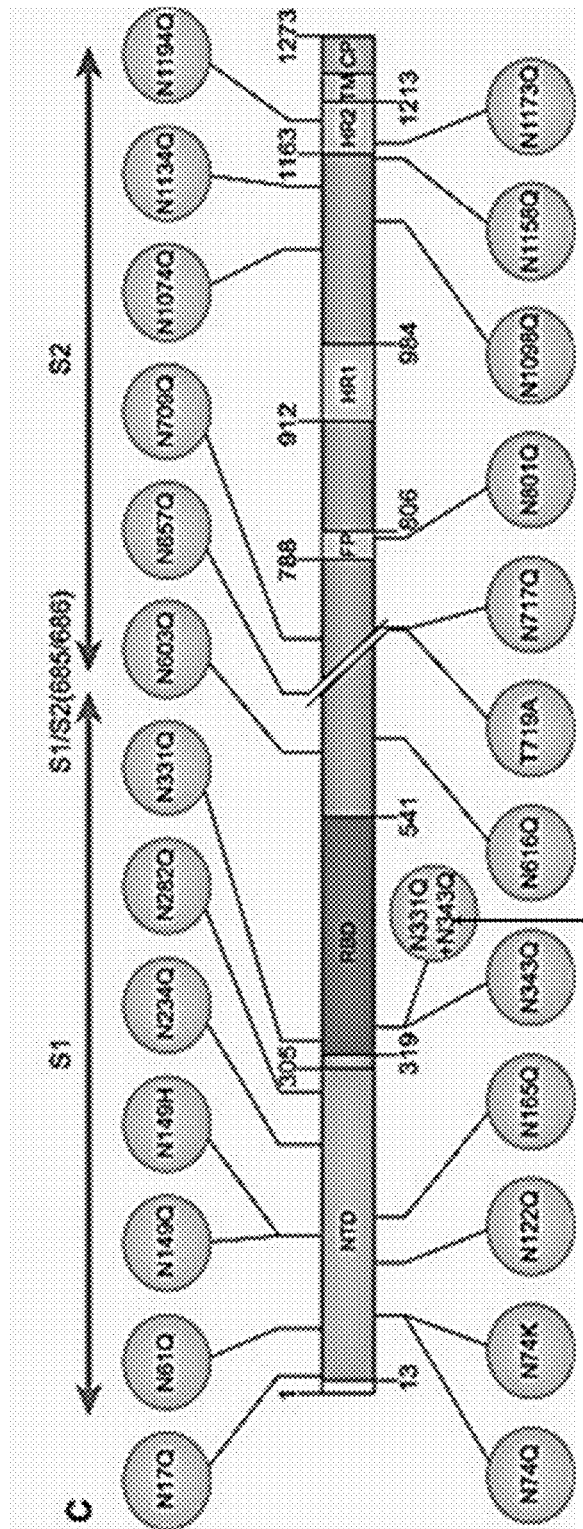

Fig. 11

MFVFLVLLPLVSSQCVNLTTRTQLPPAYTNSFTRGVYYPDKVFRSSVLHSTQDLFLPFFSNVTWFHAIH
VSGTNGTKRFDNPVLPFNDGVYFASTEKSNIIRGWIFGTTLDSKTQSLLIVNNATNVVIKVCEFQFCND
PFLGVYYHKNNKSWMESEFRVYSSANNCTFEYVSQPFLMDLEGKQGNFKNLREFVFKNIDGYFKIYSKH
TPINLVRDLPQGFSALEPLVDLPIGINITRFQTLLALHRSYLTPGDSSSGWTAGAAAYYVGYLQPRTFL
LKYNENGTITDAVDCALDPLSETKCTLKSFTVEKGIYQTSNFRVQPTESIVRFPNITNLCPFGEVFNAT
RFASVYAWNRKRISNCVADYSVLYNSASFSTFKCYGVSPTKLNDLCFTNVYADSFVIRGDEVRQIAPGQ
TGKIADYNYKLPDDFTGCVIAWNSNNLDSKVGGNYNYLYRLFRKSNLKPFERDISTEIYQAGSTPCNGV
EGFNCYFPLQSYGFQPTNGVGYQPYRVVVLSFELLHAPATVCGPKKSTNLVKNKCVNFNFNGLTGTGVL
TESNKKFLPFQQFGRDIADTTDAVRDPQTLEILDITPCSFGGVSVITPGTNTSNQVAVLYQDVNCTEVP
VAIHADQLTPTWRVYSTGSNVFQTRAGCLIGAEHVNNSYECDIPIGAGIC

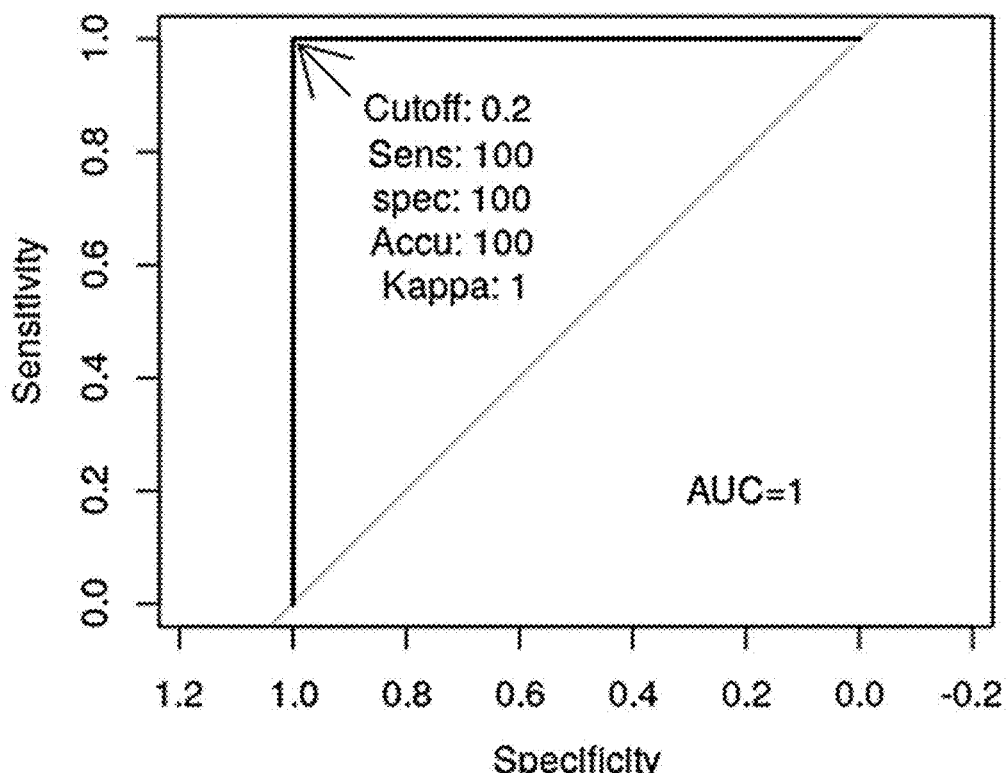
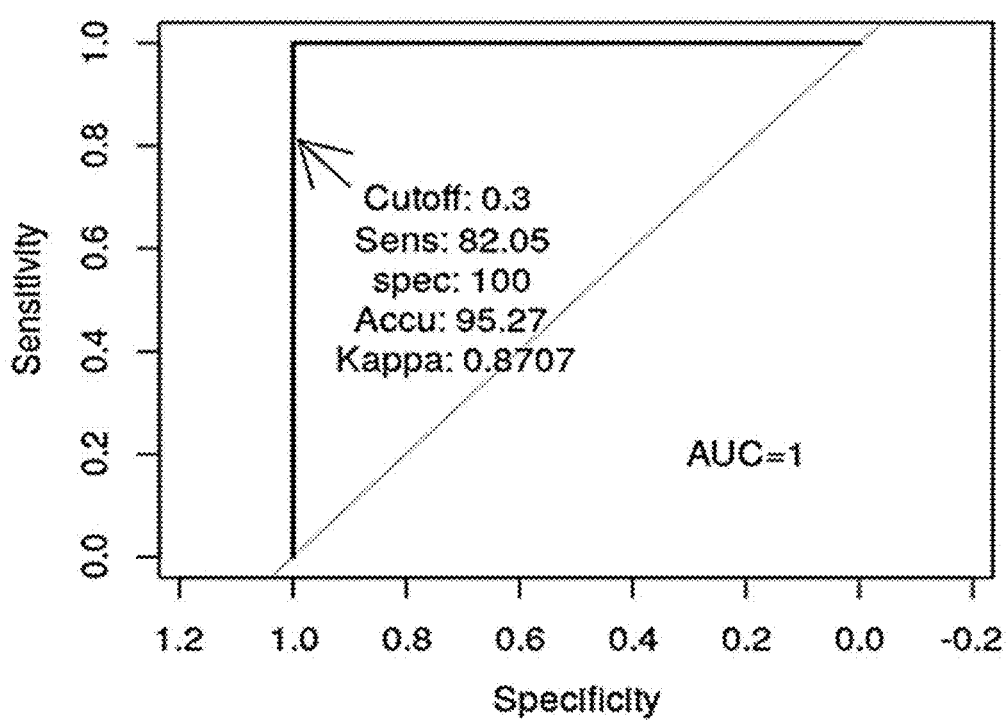
*Fig. 20*

COVID-19 SPIKE-ACE2 BINDING ASSAY FOR DRUG AND ANTIBODY SCREENING

CROSS-REFERENCE TO RELATED APPLICATION

This application is a Divisional application of U.S. patent application Ser. No. 17/141,837 entitled "COVID-19 SPIKE-ACE2 BINDING ASSAY FOR DRUG AND ANTIBODY SCREENING", filed on Jan. 5, 2021, now issued as U.S. patent Ser. No. 11/105,804 on Aug. 31, 2021, and which claims the benefit of U.S. Provisional Application No. 63/125,087 filed on Dec. 14, 2020.

SEQUENCE LISTING

This application contains a sequence listing filed in electronic form as an ASCII.txt file entitled "2208031120_ST25" created on Dec. 22, 2020. The content of the sequence listing is incorporated herein in its entirety.

TECHNICAL FIELD

The present disclosure is generally related to methods of detecting specific binding between SARS-CoV-2 spike protein and Angiotensin Converting Enzyme 2 (ACE2). The present disclosure is also generally related to kits for the performance of the methods of the disclosure.

BACKGROUND

The coronavirus disease 2019 (COVID-19) pandemic remains an urgent global public health concern, with at least 76 million cases reported and over 1.6 million deaths worldwide as of December 2020. Although several vaccines are under clinical trials, the number of infections and fatalities will continue to rise for the foreseeable future resulting in a catastrophic impact on societal health and economic development. Numerous medications have been tested for efficacy against COVID-19, notably Remdesivir®, among others, but few of these therapies have demonstrated robust efficacy in clinical trials. Therefore, hospital care of COVID-19 patients will become commonplace world-wide and treating complications such as cytokine storm and organ failure in severe cases will necessitate increase investigations into the efficacy of new treatments.

The causative agent of COVID-19, severe acute respiratory syndrome coronavirus 2 (SARS-CoV-2) is a member of the Coronaviridae family of viruses that are known to cause respiratory, hepatic, enteric, and neurologic diseases in mammals. Before 2002, coronaviruses were known only as minor human pathogens, contributing to about 15-25% of common colds. However, the emergence of a severe outbreak of SARS in 2002 caused by the novel coronavirus SARS-CoV propelled public health vigilance for diseases caused by corona viruses. To date, there are seven known coronavirus of zoonotic origin that can cause human illness, with the coronaviruses MERS-CoV, SARS-CoV, and SARS-CoV-2 identified as being causal of severe acute respiratory syndrome.

The coronavirus disease 2019 (COVID-19) is caused by the SARS-CoV-2 virus. A critical step of infection is when the virus enters human host cells, which is enabled by the interaction between the SARS-CoV-2 Spike (S) protein's receptor binding domain (RBD) on the surface of the viral particle and the Angiotensin I Converting Enzyme 2 (ACE2) receptor on the surface of human cells. Thus, the identification of small molecules, antibodies such as virus neutralizing antibodies, or other biological molecules that interfere with the formation of the S-ACE2 complex could help to develop drugs to prevent or treat COVID-19.

Currently, one test that may be used is that of Barnhizer & Faro (U.S. patent Ser. No. 10/844,442). This test is a classic Enzyme-Linked Immunoglobulin Sandwich Assay wherein a polypeptide fragment derived from a human ACE2 protein is immobilized on microtiter surfaces, contacted with a bacteria-expressed fragment of the SARS-CoV-2 Spike (S) protein's receptor binding domain (S1RBD) and, after removal of unbound S1RBD, the ACE2-S1RBD complex is detected using a labeled anti-S1RBD antibody. However, the sensitivity of this test is low, requiring microgram amounts of the primary target to obtain a detectable signal. There is, therefore, an ongoing need for a sensitive assay that does not require high amounts of the target polypeptides and is suitable for use in high-flow through identification of possible S1RBD/ACE2 binding inhibitors.

SUMMARY

One aspect of the disclosure, therefore, encompasses embodiments of a method of detecting binding between the spike-receptor binding domain (S1RBD) of the SARS-CoV-2 (Covid-19) virus and angiotensin-converting enzyme 2 (ACE2), the method comprising the steps: (a) contacting a glycosylated polypeptide derived from a spike-receptor binding domain (S1RBD) of the SARS-CoV-2 (Covid-19) virus spike (S) protein with a polypeptide derived from a mammalian ACE2, wherein the S1RBD polypeptide or the ACE2-derived polypeptide is bound to the surfaces of wells of a microtiter plate, wherein the S1RBD polypeptide is a recombinant glycosylated polypeptide expressed from a mammalian cell expression system; (b) washing the wells of unbound polypeptides; (c) either: (i) when the surface bound polypeptide is the ACE2 polypeptide, contacting the surface bound ACE2 polypeptide with the glycosylated S1RBD polypeptide, wherein the S1RBD polypeptide further comprises a tag conjugated thereto; or, (ii) when the surface bound polypeptide is the glycosylated S1RBD polypeptide, contacting the surface bound polypeptide with the ACE2 polypeptide, and then incubating the wells for a period that allows the polypeptide bound to the well surfaces to form a complex with to the polypeptide delivered thereto; (d) washing the wells of unbound polypeptides; (e) delivering to the wells from step (c)(i) a detectably labeled anti-tag-specific antibody or delivering to the wells from step (c)(ii) a detectably labeled anti-ACE2-specific antibody; (f) incubating the wells for a period to allow the antibody delivered thereto to bind to the complex formed in either step (c)(i) or (c)(ii); and (g) detecting the label on an antibody bound to the complex immobilized on the microtiter plate, thereby detecting binding of the S1RBD to the ACE2.

In some embodiments of this aspect of the invention, the polypeptide bound to wells of a microtiter plate can be an ACE2 polypeptide and is complexed in step (c)(i) to S1RBD-tag polypeptide delivered to the wells. This method can further comprise the steps: (g) repeating the assay steps (a)-(f) in the presence of a biological sample suspected of comprising SARS-CoV-2 (Covid-19) virus, wherein in step (a) the sample is added to the wells of the microtiter plate; and (h) measuring the difference between the signal from the detectable label in the absence and presence of the sample suspected of comprising SARS-CoV-2 (Covid-19) virus, wherein a reduction in the intensity of the signal generated in the presence of the compound indicates that the sample comprises SARS-CoV-2 (Covid-19) virus.

In some embodiments of this aspect of the invention the polypeptide bound to wells of a microtiter plate is a glycosylated S1RBD polypeptide expressed from a mammalian cell expression system and is complexed in step (c)(ii) to the ACE2 polypeptide delivered to the wells.

In some embodiments of this aspect of the invention the tag conjugated to the S1RBD polypeptide can be an immunoglobulin G (IgG) Fc region and the anti-tag-specific antibody can be an anti-IgG Fc-specific antibody.

In some embodiments of this aspect of the invention the S1RBD polypeptide can comprise the amino acid sequence SEQ ID NO: 1.

In some embodiments of this aspect of the invention the S1RBD polypeptide can comprise the amino acid sequence SEQ ID NO: 1 and is glycosylated at least at the N343 N-glycosylation site thereof.

In some embodiments of this aspect of the invention the label can be horse radish peroxidase (HRP).

In some embodiments of this aspect of the invention the method can further comprise the steps: (g) repeating the assay steps (a)-(f) in the presence of a compound suspected of being an inhibitor of the binding of the S1RBD polypeptide to the ACE2 polypeptide or a biological sample suspected of containing SARS-CoV-2 (Covid-19) virus or an antibody thereto, wherein in steps (c)(i) and (c)(ii) the compound is added to the wells of the microtiter plate; and (h) measuring the difference between a signal from the detectable label in the absence and presence of the compound suspected of being an inhibitor of the binding of the S1RBD polypeptide to the ACE2 polypeptide, wherein a reduction in the intensity of the signal generated in the presence of the compound indicates that the compound is an inhibitor of the S1RBD/ACE2 binding and the degree of the reduction can indicate the magnitude of the inhibition.

In some embodiments of this aspect of the invention the compound suspected of being an inhibitor of the binding of the S1RBD polypeptide to the ACE2 polypeptide can be a small molecule, an antibody, or a peptide.

In some embodiments of this aspect of the invention, the antibody can be a monoclonal antibody or in a biological sample isolated from a patient suspected of having generated anti-SARS-CoV-2 (Covid-19) virus antibodies.

Another aspect of the disclosure encompasses embodiments of a kit comprising; at least one microtiter plate comprising a plurality of wells, wherein said wells are coated with an Angiotensin Converting Enzyme 2 (ACE2) extracellular domain-derived polypeptide; a plurality of vessels, wherein said vessels can contain a wash buffer, an assay diluent, a purified glycosylated SARS-CoV-2 (Covid-19) spike protein RBD region (S1RBD)-derived polypeptide, wherein the S1RBD polypeptide is obtained by expression from a mammalian cell, and wherein the S1RBD protein has an immunoglobulin Fc tag conjugated thereto; a horse radish peroxidase-conjugated anti-immunoglobulin G (IgG) Fc-region antibody, a TMB One-Step Substrate Reagent comprising 3,3',5,5'-tetramethylbenzidine (TMB) in a buffer; and a reaction stop solution comprising about 0.2M sulfuric acid; and instructions for the use of the kit to assay the binding of the glycosylated S1RBD polypeptide to a domain of ACE2 in the absence and presence of a compound or a biological sample suspected of inhibiting said binding.

In some embodiments of the kit of the disclosure, the kit can comprise at least one microtiter plate comprising a plurality of wells, wherein said wells are coated with a glycosylated SARS-CoV-2 (Covid-19) spike protein RBD region (S1RBD)-derived polypeptide, wherein the S1RBD polypeptide is obtained by expression from a mammalian cell, a plurality of vessels, wherein said vessels can contain a wash buffer, an assay diluent, a purified extracellular domain of a recombinant ACE2 polypeptide, a horse radish peroxidase-conjugated anti-ACE2 antibody, a TMB One-Step Substrate Reagent comprising 3,3',5,5'-tetramethylbenzidine (TMB) in a buffer, and a reaction stop solution comprising about 0.2M sulfuric acid; and instruction for the use of the kit to assay the binding of the glycosylated S1RBD polypeptide to a domain of ACE2 in the absence and presence of a compound or biological sample suspected of inhibiting said binding.

BRIEF DESCRIPTION OF THE DRAWINGS

Further aspects of the present disclosure will be more readily appreciated upon review of the detailed description of its various embodiments, described below, when taken in conjunction with the accompanying drawings.

Untreated and deglycosylated S1RBD proteins were coated on a 96-well plate respectively. A series of concentrations (0, 20, 40, 60, 80, 100 ng/ml) of ACE2 protein were added into the wells and bound ACE2 protein was detected using anti-ACE2 antibody and HRP conjugated secondary antibody. PNGase F treated S1RBD protein showed no binding to ACE2 protein.

Figure 8:
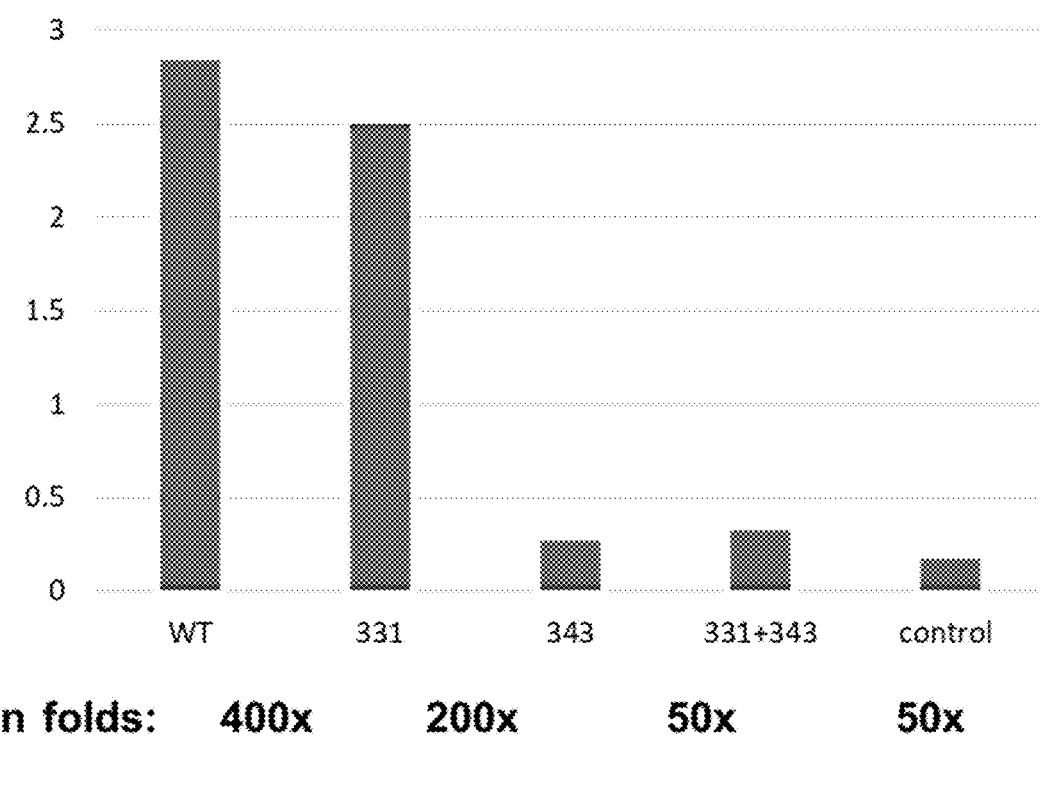

FIG. 8 shows that N-linked S1RBD protein glycosylation at the N343 position of the S1 domain of the spike protein having the amino acid sequence SEQ ID NO: 1 is essential for binding to ACE2. The S-ACE2 interaction was assessed using wildtype and mutant of SARS-CoV-2 S1RBD. Mammalian cell-expressed wildtype and three mutant S1RBD proteins, (N331Q, N343Q and N331Q/N343Q) were applied to the binding assay of the disclosure. Bound ACE2 protein was detected using anti ACE2 antibody and HRP conjugated secondary antibody.

FIG. 9 shows infectivity analysis of a wild type and three glycosylation mutant pseudoviruses rVSV pseudovirus bearing SARS-COV-2 wild type and three mutants, N331Q, N343Q, and N331/343Q of the RBD of the spike protein S1 region of the spike protein were used to drive entry into A549 cells or Vero cells. At 24 h post infection, pseudotype entry was analyzed by determining luciferase activity in cell lysates, and the luminescence relative ratio to the wild type pseudovirus.

Figure 10A:
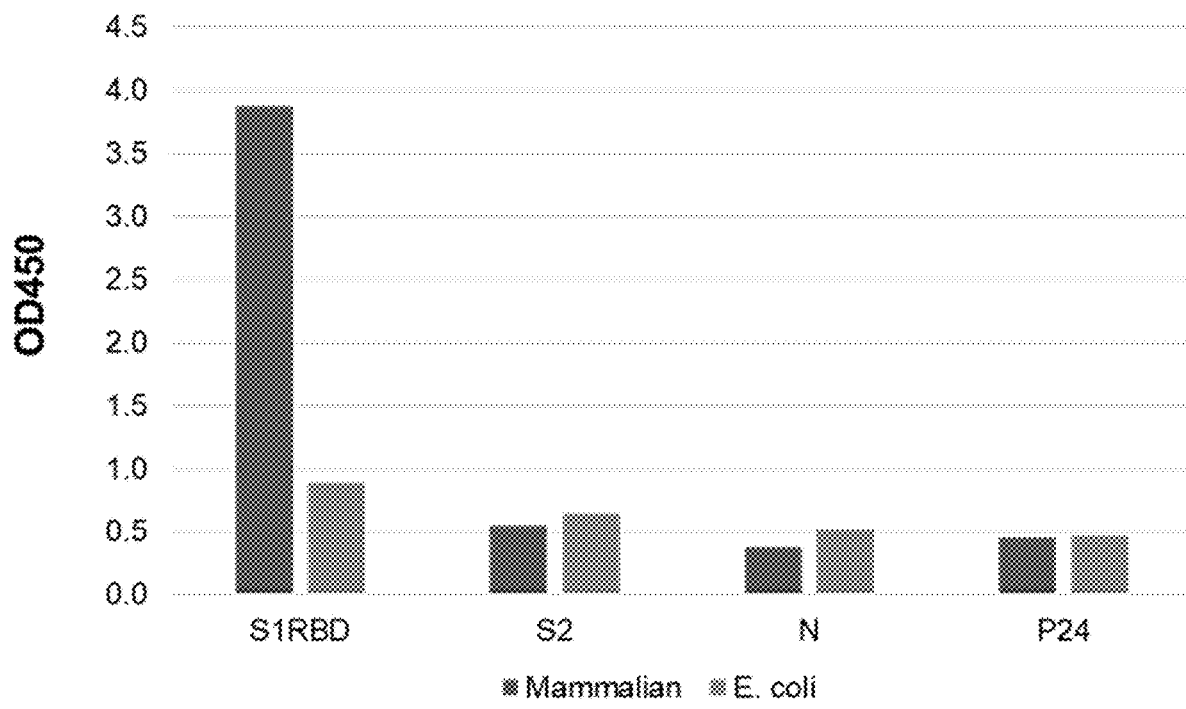
Figure 10B:
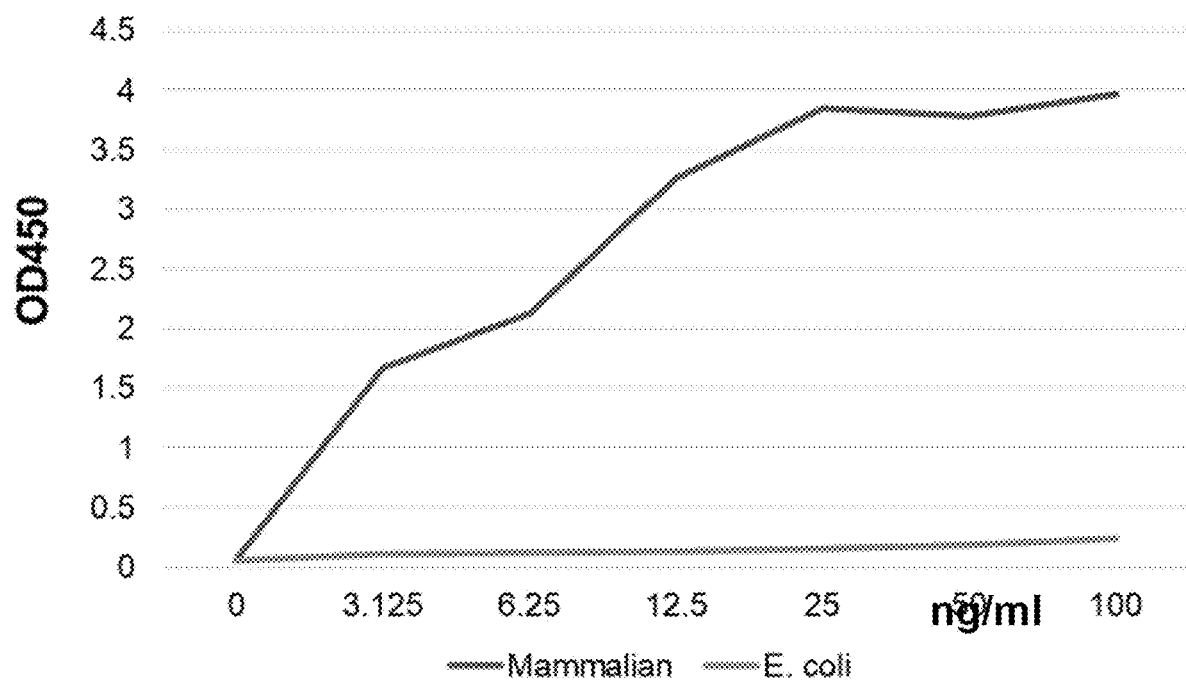

FIGS. 10A and 10B illustrate that mammalian cell-expressed SARS-COV-2 S1RBD has a better binding activity to ACE2 than does E coli-expressed S1RBD in vitro.

FIG. 10A shows the ACE2 binding activity of mammalian and E coli expressed proteins of SARS-COV-2: S1RBD, S1 and S2 proteins was detected using ACE-2 binding assay. The mammalian cell-expressed S1RBD shows the best S1RBD-ACE2 binding activity compared to E coli-expressed S1RBD as well as S1 and S2. Nucleocapsid protein (N) and HIV p24 (P24) were served as controls.

FIG. 10B shows the S1RBD-ACE2 binding curve. The mammalian cell-expressed S1RBD shows the dose dependent binding activity (0, 3.125, 6.25, 12.5, 25, 50, and 100 ng/ml) compared to the E coli-expressed S1RBD.

FIG. 11 illustrates mutations of the putative glycosylation sites, including N to Q mutations at 22 putative glycosylation sites, a combination of two glycosylation site mutations in RBD, and three naturally occurring variants, N74K, N149H, and T719A, with ablated glycosylation sites.

FIG. 12 shows the amino acid sequence (SEQ ID NO: 1) of the SARS-CoV-2 Spike and the S1 receptor binding domain (RBD) expressed from a mammalian cell expression system.

Figure 13:
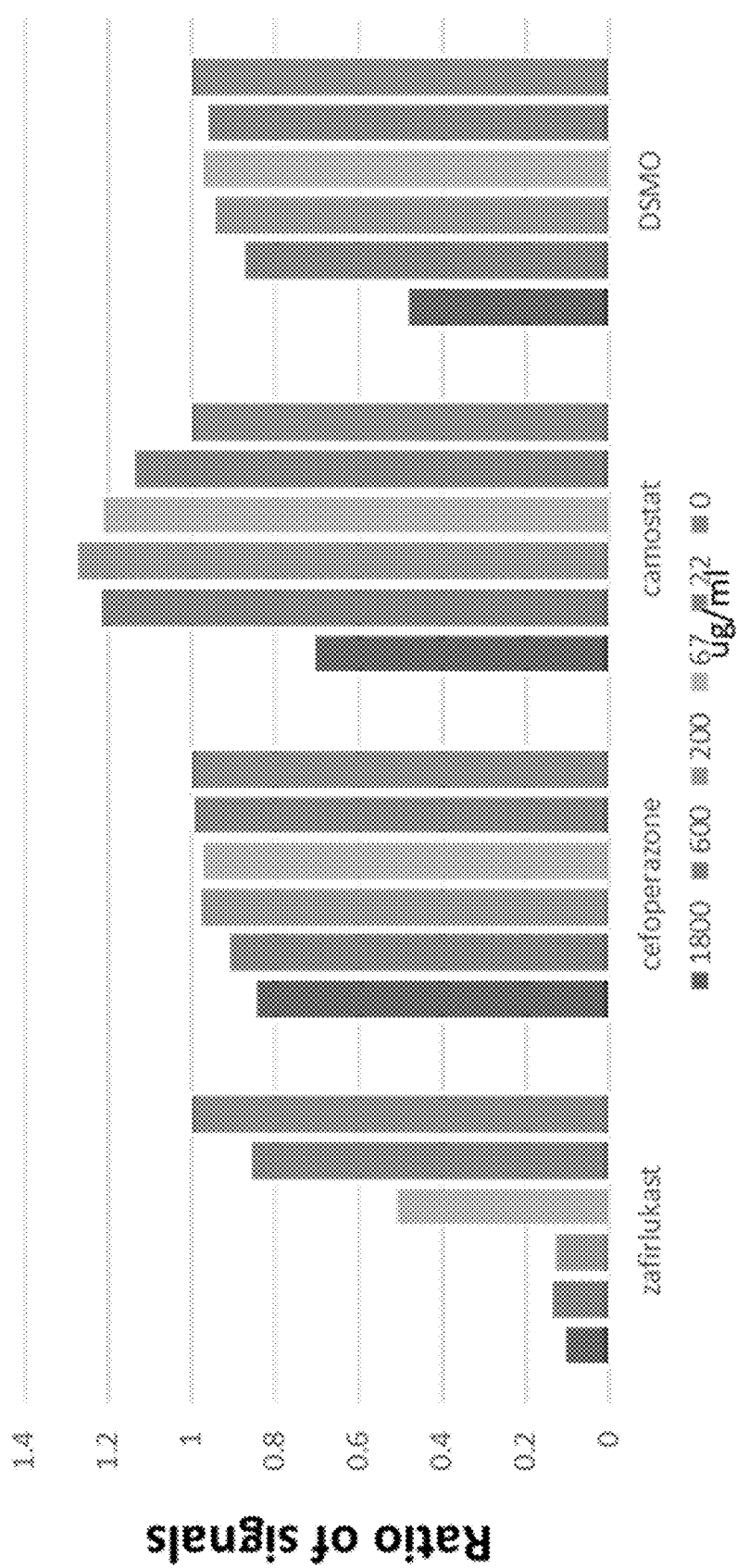

FIG. 13 illustrates the ability of the assay method of the disclosure to identify small molecule inhibitors of the binding of ACE2 and S1RBD. Zafirlukast and cefoperazone, two potent inhibitors of S1RBD-ACE2 binding selected by virtual screening, were tested using the S1RBD-ACE2 binding assay (cat #CoV-SACE2-1). Camostat Mesilate, a potent serine protease inhibitor, and DMSO were served as negative controls. A serial dilution (1800, 600, 200, 67 22, 0 ug/ml) of each compound were mixed with ACE2 protein, and then added to S1RBD protein coated 96-well plate. Unbound ACE2 was removed with washing, and bound ACE2 was detected by an anti-ACE2 antibody and an HRP-conjugated secondary antibody. The intensity of the yellow color was then measured at 450 nm, and ratio of signals (OD) of sample vs. ACE2 alone control was calculated and shown.

Figure 14:
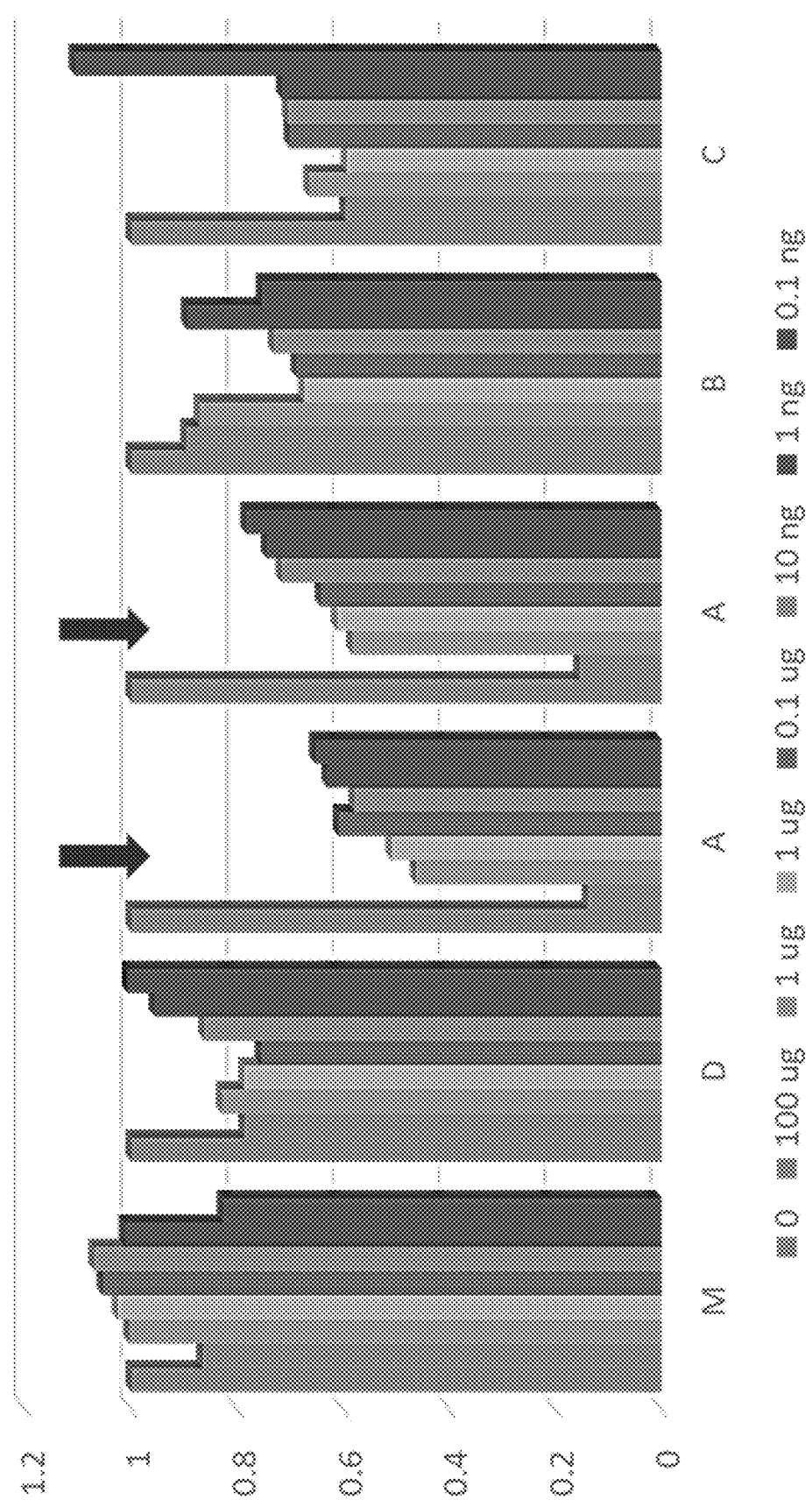

FIG. 14 illustrates, using a pseudovirus luciferase assay, that Compound A (Zafirlukast) identified using the S1RBD-ACE2 binding assay has a blocking effect on pseudovirus entry into host A549 cells.

Figure 15:
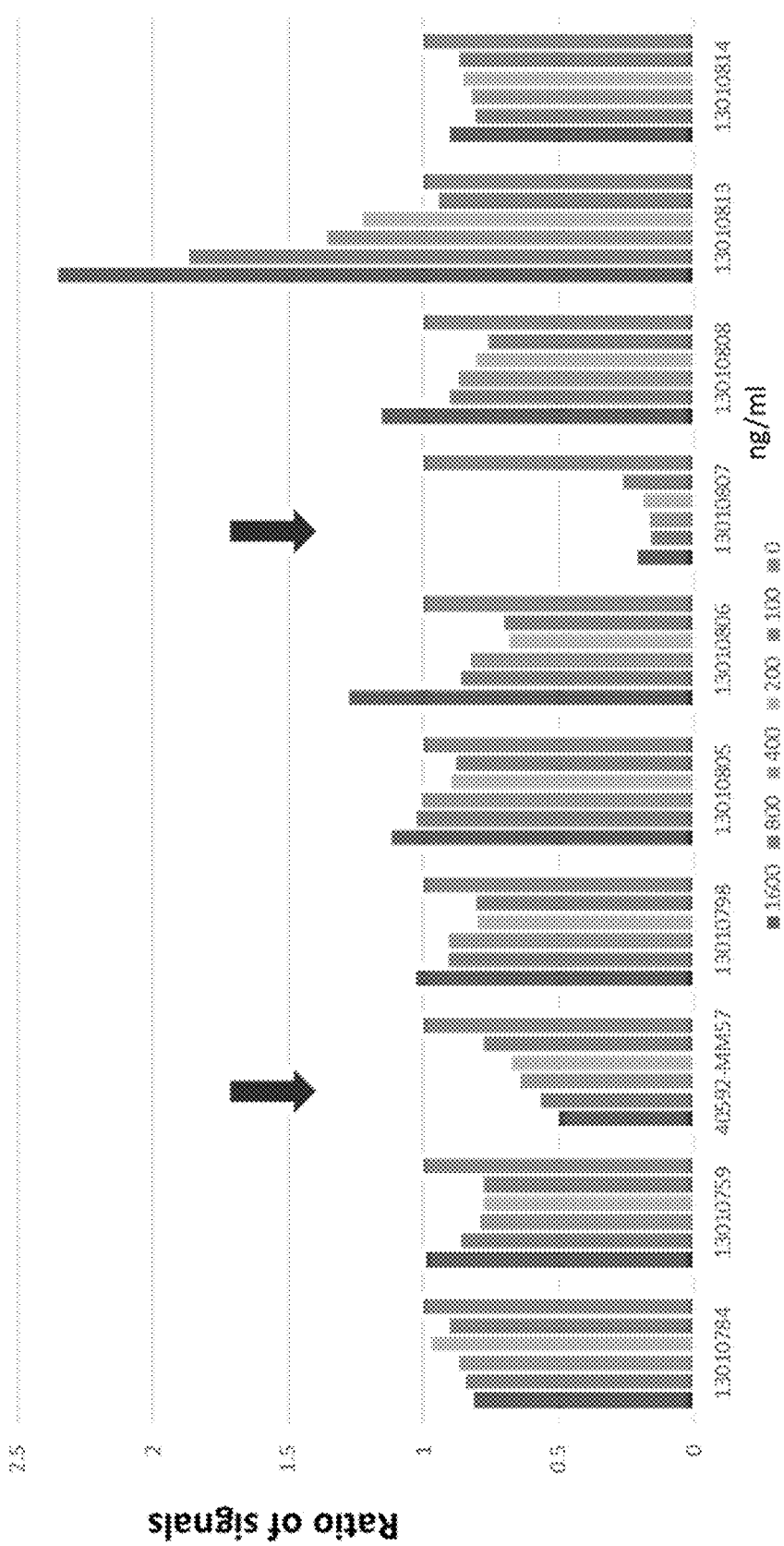

FIG. 15 illustrates the ability of the assay method of the disclosure to identify putative monoclonal antibody inhibitors of the binding of ACE2 and S1RBD. Monoclonal antibodies against S1RBD were tested using the S1RBD-ACE2 binding assay (cat #CoV-SACE2-1). A serial dilution (1600, 800, 400, 200, 100, 0 ng/ml) of each antibody were mixed with ACE2 protein, and then added to S1RBD protein coated 96-well plate. Unbound ACE2 was removed with washing, and bound ACE2 was detected by an anti-ACE2 antibody and an HRP-conjugated secondary antibody. The intensity of the yellow color was then measured at 450 nm, and ratio of signals of sample vs. ACE2 alone control was calculated and shown.

Figure 16:
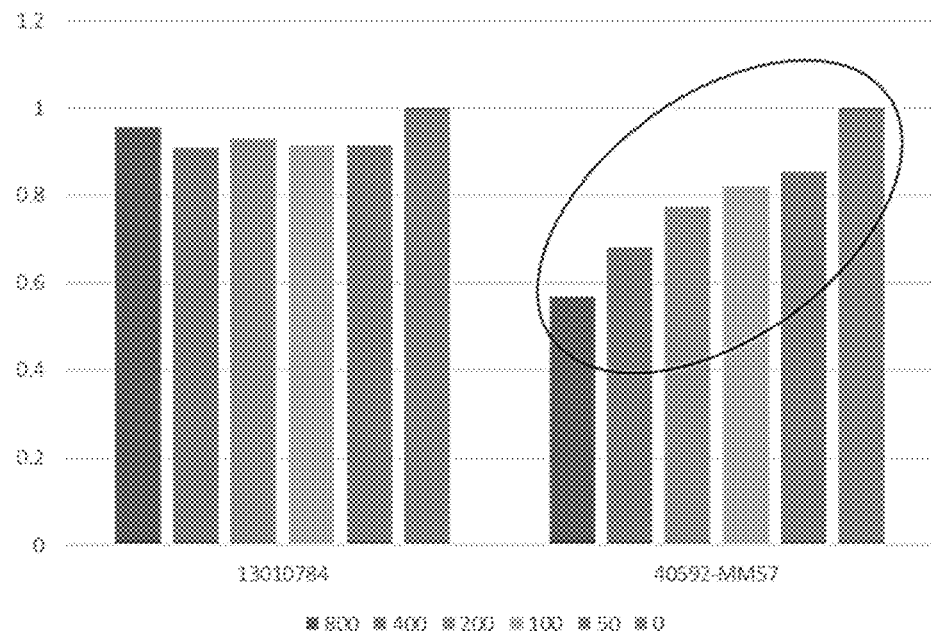

FIG. 16 illustrates the ability of the assay method of the disclosure to identify putative monoclonal antibody inhibitors of the binding of ACE2 and S1RBD.

Figure 17:
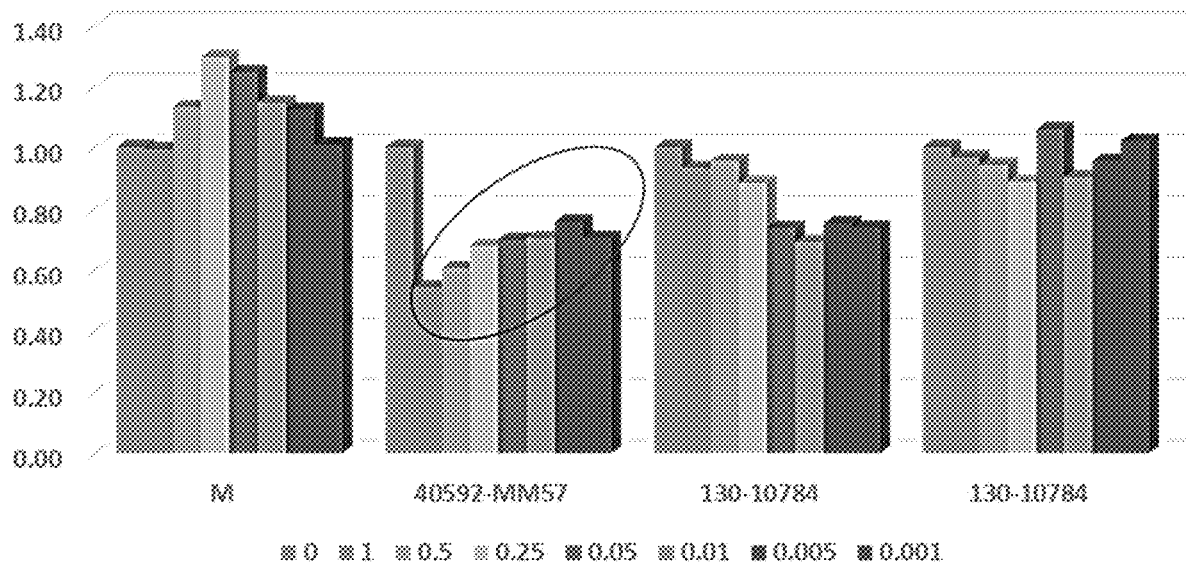

FIG. 17 illustrates, using a pseudovirus luciferase assay, that putative monoclonal antibodies identified as inhibiting S1RBD/ACE2 binding in vitro have a blocking effect on pseudovirus entry into host A549 cells.

Figure 18:
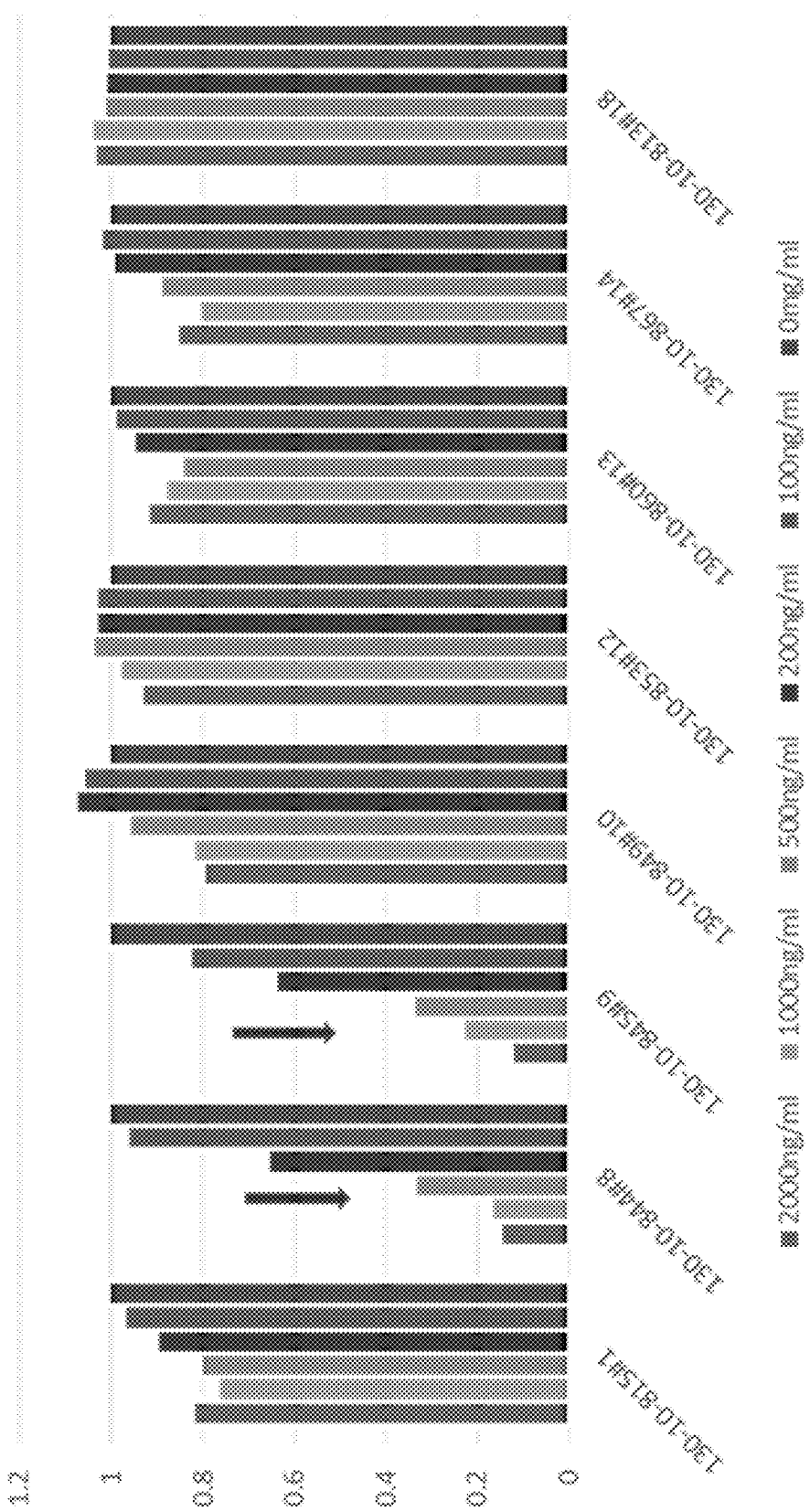

FIG. 18 illustrates the ability of the assay method of the disclosure to identify putative monoclonal antibody inhibitors of the binding of ACE2 and S1RBD. Monoclonal (mAb) screening for S1-RBD Covid19 Protein using S1-RBD polypeptide coating the wells of a microtiter plate.

Figure 19:
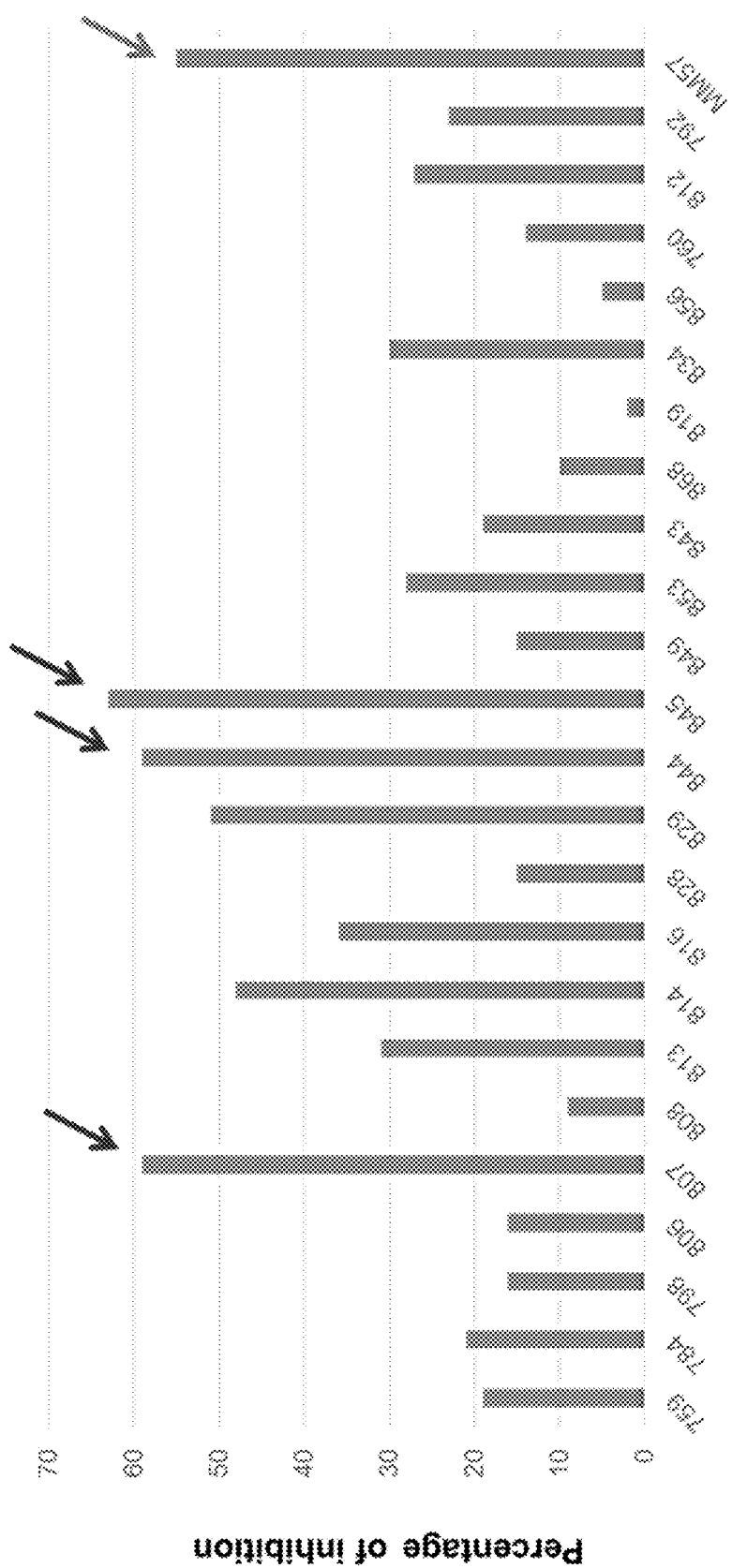

FIG. 19 illustrates, using a pseudovirus luciferase assay, that putative monoclonal antibodies identified as inhibiting S1RBD/ACE2 binding in vitro have a blocking effect on pseudovirus entry into host A549 cells. Pseudoviruses harboring the SARS-COV-2 spike viral surface glycosylation protein (S1RBD) were incubated with different antibodies at the concentration of 2 μg/ml at 37° C. for 1 h and inoculated into A549 cells. At 24 h post-infection, pseudotype entry was measured by determining luciferase activity in cell lysates, and the luminescence relative ratio to the "zero" concentration data is shown.

FIG. 20 illustrates the evaluation of the diagnostic performance of the ACE2 binding assays of the disclosure in detecting COVID19-specific neutralizing antibody in serum.

DETAILED DESCRIPTION

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, dimensions, frequency ranges, applications, or the like, as such can vary. It is also to be understood that the terminology used herein is for purposes of describing particular embodiments only, and is not intended to be limiting. It is also possible in the present disclosure that steps can be executed in different sequence, where this is logically possible. It is also possible that the embodiments of the present disclosure can be applied to additional embodiments involving measurements beyond the examples described herein, which are not intended to be limiting. It is furthermore possible that the embodiments of the present disclosure can be combined or integrated with other measurement techniques beyond the examples described herein, which are not intended to be limiting.

It should be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. Further, documents or references cited in this text, in a Reference List before the claims, or in the text itself; and each of these documents or references ("herein cited references"), as well as each document or reference cited in each of the herein-cited references (including any manufacturer's specifications, instructions, etc.) are hereby expressly incorporated herein by reference.

Prior to describing the various embodiments, the following definitions are provided and should be used unless otherwise indicated.

Abbreviations

ELISA, Enzyme Linked Immunoglobulin Sandwich Assay; TMB, 3,3,5,5'-tetramethylbenzidine; SARS-CoV-2, Severe Acute Respiratory Syndrome Coronavirus 2; COVID-19, coronavirus disease 2019; RBD receptor binding domain.

Definitions

The term "specific binding" as used herein refers to the specific recognition of one molecule, of two different molecules, compared to substantially less recognition of other molecules. Generally, the molecules have areas on their surfaces or in cavities giving rise to specific recognition between the two molecules. Exemplary of specific binding are antibody-antigen interactions.

The term "antibody" as used herein refers to an immunoglobulin which specifically binds to and is thereby defined as complementary with a particular spatial and polar organization of another molecule. The antibody can be monoclonal, polyclonal, or a recombinant antibody, and can be prepared by techniques that are well known in the art such as immunization of a host and collection of sera (polyclonal) or by preparing continuous hybrid cell lines and collecting the secreted protein (monoclonal), or by cloning and expressing nucleotide sequences, or mutagenized versions thereof, coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, IgY, etc. Fragments thereof may include Fab, Fv and F(ab')2, Fab', scFv, and the like. In addition, aggregates, polymers, and conjugates of immunoglobulins or their fragments can be used where appropriate so long as binding affinity for a particular molecule is maintained.

Antibodies may be derived from any source, including, but not limited to, murine spp., rat, rabbit, chicken, human, or any other origin (including humanized antibodies). Techniques for the generation of antibodies that can specifically recognize and bind to are known in the art.

The term "antigen" as used herein refers to any entity that binds to an antibody and induces at least one shared conformational epitope on the antibody. Antigens can be proteins, peptides, antibodies, small molecules, lipid, carbohydrates, nucleic acid, and allergens. An antigen may be in its pure form or in a sample in which the antigen is mixed with other components. In particular, the methods of the present disclosure are intended to detect human or animal immunoglobulins that specifically recognize and bind to epitopes of the S and/or N polypeptides of the SARS-CoV-2 virus.

The term "Severe Acute Respiratory Syndrome Coronavirus 2 (SARS-CoV-2)" as used herein refers to is the strain of coronavirus that causes coronavirus disease 2019 (COVID-19), the respiratory illness responsible for the COVID-19 pandemic. Colloquially known as simply the coronavirus, it was previously referred to by its provisional name, 2019 novel coronavirus (2019-nCoV), and has also been called human coronavirus 2019 (HCoV-19 or hCoV-19). SARS-CoV-2 is a Baltimore class IV positive-sense single-stranded RNA virus that is contagious in humans. It is the successor to SARS-CoV-1, the strain that caused the 2002-2004 SARS outbreak.

Each SARS-CoV-2 virion is 50-200 nm in diameter. Like other coronaviruses, SARS-CoV-2 has four structural proteins, known as the S (spike), E (envelope), M (membrane), and N (nucleocapsid) proteins; the N protein holds the RNA genome, and the S, E, and M proteins together create the viral envelope. The spike protein, which has been imaged at the atomic level is responsible for allowing the virus to attach to and fuse with the membrane of a host cell; specifically, its S1 subunit catalyzes attachment, the S2 subunit fusion.

SARS-CoV-2 has sufficient affinity to the receptor angiotensin converting enzyme 2 (ACE2) on human cells to use them as a mechanism of cell entry. Studies have shown that SARS-CoV-2 has a higher affinity to human ACE2 than the original SARS virus strain.

Initial spike protein priming by transmembrane protease, serine 2 (TMPRSS2) is essential for entry of SARS-CoV-2. After a SARS-CoV-2 virion attaches to a target cell, the cell's protease TMPRSS2 cuts open the spike protein of the virus, exposing a fusion peptide in the S2 subunit, and the host receptor ACE2. After fusion, an endosome forms around the virion, separating it from the rest of the host cell. The virion escapes when the pH of the endosome drops or when cathepsin, a host cysteine protease, cleaves it. The virion then releases RNA into the cell and forces the cell to produce and disseminate copies of the virus, which infect more cells.

The term "biological sample" as used herein can refer to a sample derived from blood, preferably peripheral (or circulating) blood. A blood sample may be, for example, whole blood, blood obtained by a finger prick or a dried blood sample, plasma, serum, or a solubilized preparation of such fluids wherein the cell components have been lysed to release intracellular contents into a buffer or other liquid medium.

The terms "binding" as used herein refers to the non-covalent interactions of the type between a first polypeptide molecule and a second polypeptide. The strength, or affinity of binding interactions can be expressed in terms of the dissociation constant ($K_d$) of the interaction, wherein a smaller $K_d$ represents a greater affinity. Binding properties of selected polypeptides can be quantified using methods well known in the art. One such method entails measuring the rate of complex formation and dissociation of the two interacting polypeptides, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$.

The term "surface" as used herein refers to a solid support such as the surface of the bottom of a well of a microtiter plate, which are particularly useful for in vitro assays. Such solid supports might be porous or nonporous, planar or nonplanar and include, but are not limited to, glass, cellulose, polyacrylamide, nylon, polystyrene, polyvinyl chloride or polypropylene supports. As another example, the polypeptides of the invention can usefully be attached to the surface of a microtiter plate for ELISA.

The term "tag" as used herein refers to a moiety conjugated to a molecule such as a peptide or a polypeptide that it is desirable to label but does not necessarily have the label attached. A tag can allow a label or labelled moiety to specifically bind to the tag. A tag may be a small molecule to which the labeled moiety can bind, a larger molecule such as a peptide, e.g. a hexa-histidine chain, a polypeptide or combination of polypeptide chains such as, but not limited to, an Fc region of an antibody any of which may be selectively bound by a suitably selected labeled moiety such as, but not limited to an anti-Fc region antibody By "detectably labeled" is meant that a polypeptide or a fragment thereof, contains a moiety that is elicits a physical or chemical response, a fluorophore or dye, and which can be observed or detected by the naked eye or by means of instrumentation such as, without limitation, colorimeters, UV spectrophotometers and the like.

The term "detectable moiety" as used herein refers to a label molecule (isotopic or non-isotopic) which is incorporated indirectly or directly into a liposomal nanoparticle according to the disclosure, wherein the label molecule facilitates the detection of the nanoparticle in which it is incorporated. Thus, "detectable moiety" is used synonymously with "label molecule". Label molecules, known to those skilled in the art as being useful for detection, include chemiluminescent or fluorescent molecules. Various fluorescent molecules are known in the art which are suitable for use to label a nucleic acid for the method of the present invention. The protocol for such incorporation may vary depending upon the fluorescent molecule used. Such protocols are known in the art for the respective fluorescent molecule.

The term "dye" as used herein refers to any reporter group whose presence can be detected by its light absorbing or light emitting properties. For example, Cy5 is a reactive water-soluble fluorescent dye of the cyanine dye family. Cy5 is fluorescent in the red region (about 650 to about 670 nm). It may be synthesized with reactive groups on either one or both of the nitrogen side chains so that they can be chemically linked to either nucleic acids or protein molecules. Labeling is done for visualization and quantification purposes. Cy5 is excited maximally at about 649 nm and emits maximally at about 670 nm, in the far-red part of the spectrum; quantum yield is 0.28. FW=792. Suitable fluorophores(chromes) for the probes of the disclosure may be selected from, but not intended to be limited to, fluorescein isothiocyanate (FITC, green), cyanine dyes Cy2, Cy3, Cy3.5, Cy5, Cy5.5 Cy7, Cy7.5 (ranging from green to near-infrared), Texas Red, and the like. Derivatives of these dyes for use in the embodiments of the disclosure may be, but are not limited to, Cy dyes (Amersham Bioscience), Alexa Fluors (Molecular Probes Inc.), HILYTE™ Fluors (AnaSpec), and DYLITE™ Fluors (Pierce, Inc).

The term "fluorophore" as used herein refers to any reporter group whose presence can be detected by its light emitting properties.

The term "immobilized on a solid support" as used herein refers to a polypeptide attached to a substrate at a particular location so that it may be subjected to washing or other physical or chemical manipulation without being dislodged. A number of solid supports and immobilizing methods are known in the art, and may be used in the methods of this disclosure.

The terms "expressed" and "expression" as used herein refer to the transcription from a gene to give an RNA nucleic acid molecule at least complementary in part to a region of one of the two nucleic acid strands of the gene. The term "expressed" or "expression" as used herein also refers to the translation from said RNA nucleic acid molecule to give a protein, an amino acid sequence or a portion thereof.

The term "fragment" of a protein or nucleic acid as used herein refers to any portion of the amino acid sequence.

The term "immunoglobulin" as used herein refers to a class of proteins that exhibit antibody activity and bind to other molecules (e.g., antigens and certain cell-surface receptors) with a high degree of specificity. Immunoglobulins can be divided into five classes: IgM, IgG, IgA, IgD, and IgE. IgG is the most abundant antibody class in the body and assumes a twisted "Y" shape configuration. With the exception of the IgMs, immunoglobulins are composed of four peptide chains that are linked by intrachain and interchain disulfide bonds. IgGs are composed of two polypeptide heavy chains (H chains) and two polypeptide light chains (L chains) that are coupled by non-covalent disulfide bonds.

The light and heavy chains of immunoglobulin molecules are composed of constant regions and variable regions. For example, the light chains of an IgG1 molecule each contain a variable domain (V$_L$) and a constant domain (C$_L$). The heavy chains each have four domains: an amino terminal variable domain (V$_H$), followed by three constant domains (C$_H$1, C$_H$2, and the carboxy terminal C$_H$3). A hinge region corresponds to a flexible junction between the C$_H$1 and C C$_H$2 domains. Papain digestion of an intact IgG molecule results in proteolytic cleavage at the hinge and produces an Fc fragment that contains the C$_H$2 and C$_H$3 domains, as well as two identical Fab fragments that each contain a C$_H$1 C$_L$, V$_H$, and V$_L$ domain. The Fc fragment has complement- and tissue-binding activity. The Fab fragments have antigen-binding activity Immunoglobulin molecules can interact with other polypeptides through a cleft within the C$_H$2-C$_H$3 domain. This "C$_H$2-C$_H$3 cleft" typically includes the amino acids at positions 251-255 within the C$_H$2 domain and the amino acids at positions 424-436 within the C$_H$3 domain. As used herein, numbering is with respect to an intact IgG molecule as in Kabat et al. (Sequences of Proteins of Immunological Interest, 5th ed., Public Health Service, U.S. Department of Health and Human Services, Bethesda, Md.). The corresponding amino acids in other immunoglobulin classes can be readily determined by those of ordinary skill in the art.

The Fc region can bind to a number of effector molecules and other proteins, including the cellular Fe Receptor that provides a link between the humoral immune response and cell-mediated effector systems (Hamano et al., (2000) *J. Immunol.* 164: 6113-6119; Coxon et al., (2001) *Immunity* 14: 693-704; Fossati et al., (2001) *Eur. J. Clin. Invest.* 31: 821-831). The FC□ receptors are specific for IgG molecules, and include FcγRI, FcγRIIa, FcγRIIb, and FcγRIII. These isotypes bind with differing affinities to monomeric and immune-complexed IgG.

The term "polypeptide" includes proteins and fragments thereof. Polypeptides are disclosed herein as amino acid residue sequences.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from said RNA nucleic acid molecule to give a protein, an amino acid sequence or a portion thereof.

The term "recombinant" as used herein, and referring to a nucleic acid molecule, means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide The term "engineered protein" as used herein refers to a non-naturally-occurring polypeptide. The term encompasses, for example, a polypeptide that comprises one or more changes, including additions, deletions or substitutions, relative to a naturally occurring polypeptide, wherein such changes were introduced by recombinant DNA techniques. The term also encompasses a polypeptide that comprises an amino acid sequence generated by man, an artificial protein, a fusions protein, and a chimeric polypeptide. Once expressed, recombinant peptides, polypeptides and proteins can be purified according to standard procedures known to one of ordinary skill in the art, including ammonium sulfate precipitation, affinity columns, column chromatography, gel electrophoresis and the like. Substantially pure compositions of about 50 to 99% homogeneity are preferred, and 80 to 95% or greater homogeneity are most preferred for use as therapeutic agents.

The term "detectable label" as used herein refers to a moiety attached to a specific binding partner, such as an antibody or an analyte, e.g., to render the reaction between members of a specific binding pair, such as an antibody and an analyte, detectable, and the specific binding partner, e.g., antibody or analyte, so labeled is referred to as "detectably labeled." Thus, the term "labeled binding protein" as used herein, refers to a protein with a label incorporated that provides for the identification of the binding protein. In an embodiment, the label is a detectable marker that can produce a signal that is detectable by visual or instrumental means, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides, chromogens, fluorescent labels (e.g., FITC, rhodamine, and lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, and epitope tags); and magnetic agents, such as gadolinium chelates. Representative examples of labels commonly employed for immunoassays include moieties that produce light, e.g., acridinium compounds, and moieties that produce fluorescence, e.g., fluorescein. Other labels are described herein. In this regard, the moiety itself may not be detectably labeled but may become detectable upon reaction with yet another moiety. Use of "detectably labeled" is intended to encompass the latter type of detectable labeling.

The term "monoclonal antibody" or "mAb" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each mAb is directed against a single determinant on the antigen. The modifier "monoclonal" is not to be construed as requiring production of the antibody by any particular method.

The term "recombinant" as used herein, and referring to a nucleic acid molecule, means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide the term "engineered protein" as used herein refers to a non-naturally-occurring polypeptide. The term encompasses, for example, a polypeptide that comprises one or more changes, including additions, deletions or substitutions, relative to a naturally occurring polypeptide, wherein such changes were introduced by recombinant DNA techniques. The term also encompasses a polypeptide that comprises an amino acid sequence generated by man, an artificial protein, a fusions protein, and a chimeric polypeptide. Once expressed, recombinant peptides, polypeptides and proteins can be purified according to standard procedures known to one of ordinary skill in the art, including ammonium sulfate precipitation, affinity columns, column chromatography, gel electrophoresis and the like. Substantially pure compositions of about 50 to 99% homogeneity are preferred, and 80 to 95% or greater homogeneity are most preferred for use as therapeutic agents.

The term "small molecule" as used herein refers to an organic compound, including an organometallic compound, of a molecular weight less than about 2 kDa, that is not a polynucleotide, a polypeptide, a polysaccharide, or a synthetic polymer composed of a plurality of repeating units.

The term "polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric. Use of "polypeptide" herein is intended to encompass polypeptide and fragments and variants (including fragments of variants) thereof, unless otherwise stated.

The term "sample," as used herein, is used in its broadest sense. A "biological sample," as used herein, includes, but is not limited to, any quantity of a substance from a living thing or formerly living thing. Such living things include, but are not limited to, humans, mice, rats, monkeys, dogs, rabbits and other animals. Such substances include, but are not limited to, blood, (e.g., whole blood), plasma, serum, urine, amniotic fluid, synovial fluid, endothelial cells, leukocytes, monocytes, other cells, organs, tissues, bone marrow, lymph nodes and spleen.

The term "control" refers to a composition known to not contain analyte ("negative control") or to contain analyte ("positive control"). A positive control can comprise a known concentration of analyte. "Control," "positive control," and "calibrator" may be used interchangeably herein to refer to a composition comprising a known concentration of analyte. A "positive control" can be used to establish assay performance characteristics and is a useful indicator of the integrity of reagents (e.g., analytes).

The terms "specific" and "specificity" as used herein are in the context of an interaction between members of a specific binding pair (e.g., an antigen (or fragment thereof) and an antibody (or antigenically reactive fragment thereof)) refer to the selective reactivity of the interaction. The phrase "specifically binds to" and analogous phrases refer to the ability of antibodies (or antigenically reactive fragments thereof) to bind specifically to analyte (or a fragment thereof) and not bind specifically to other entities.

The term "Angiotensin-Converting Enzyme 2 (ACE2)" as used herein is an enzyme attached to the cell membranes of cells located in the lungs, arteries, heart, kidney, and intestines. ACE2 lowers blood pressure by catalyzing the hydrolysis of angiotensin II (a vasoconstrictor peptide) into angiotensin (1-7) (a vasodilator). ACE2 counters the activity of the related angiotensin-converting enzyme (ACE) by reducing the amount of angiotensin-II and increasing Ang(1-7), making it a promising drug target for treating cardiovascular diseases. ACE2 serves as the entry point into cells for some coronaviruses, including HCoV-NL63, SARS-CoV, and SARS-CoV-2.

Angiotensin-converting enzyme 2 is a zinc-containing metalloenzyme located on the surface of endothelial and other cells. ACE2 protein contains an N-terminal peptidase M2 domain and a C-terminal collectrin renal amino acid transporter domain. ACE2 is a single-pass type I membrane protein, with its enzymatically active domain exposed on the surface of cells in the lungs and other tissues. The extracellular domain of ACE2 is cleaved from the transmembrane domain by another enzyme known as sheddase, and the resulting soluble protein is released into the bloodstream and ultimately excreted as urine.

One fragment of the ACE2 advantageous in the methods of the disclosure is isolated from the human AVE2 having the Accession No: Q9BYF1 and is the expressed Region Gln18-Ser740 (Extracellular domain) (SEQ ID NO: 2).

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

The term "lateral flow tests as used herein, also known as lateral flow immunochromatographic assays, refers to devices intended to detect the presence of a target substance in a liquid sample without the need for specialized and costly equipment. These tests are widely used in medical diagnostics for home testing, point of care testing, or laboratory use. These tests are simple, economic and generally show results in around 5-30 minutes.

Lateral flow tests operate on the same principles as the enzyme-linked immunosorbent assays (ELISA). Tests run the liquid sample along the surface of a pad with reactive molecules that show a visual positive or negative result. The pads are based on a series of capillary beds, such as pieces of porous paper, microstructured polymer. The pads have the capacity to transport fluid (e.g., urine, blood, saliva) spontaneously.

The sample pad acts as a sponge and holds an excess of sample fluid. Once soaked, the fluid flows to the second conjugate pad in which can be stored freeze dried bio-active particles called conjugates (see below) in a salt-sugar matrix. A conjugate pad contains all the reagents required for an optimized reaction between the target molecule (e.g., ACE2 protein) and its partner (e.g., S1RBD-tag polypeptide) that has been immobilized on the particle's surface. This marks target particles as they pass through the pad and continue across to the test and control lines. The test line shows a signal. The control line contains affinity ligands (in the context of the assays of the disclosure, an anti-tag antibody) that show whether the sample has flowed through and the bio-molecules in the conjugate pad are active. After passing these reaction zones, the fluid enters the final porous material, the wick, that simply acts as a waste container.

Discussion

Figure 1:
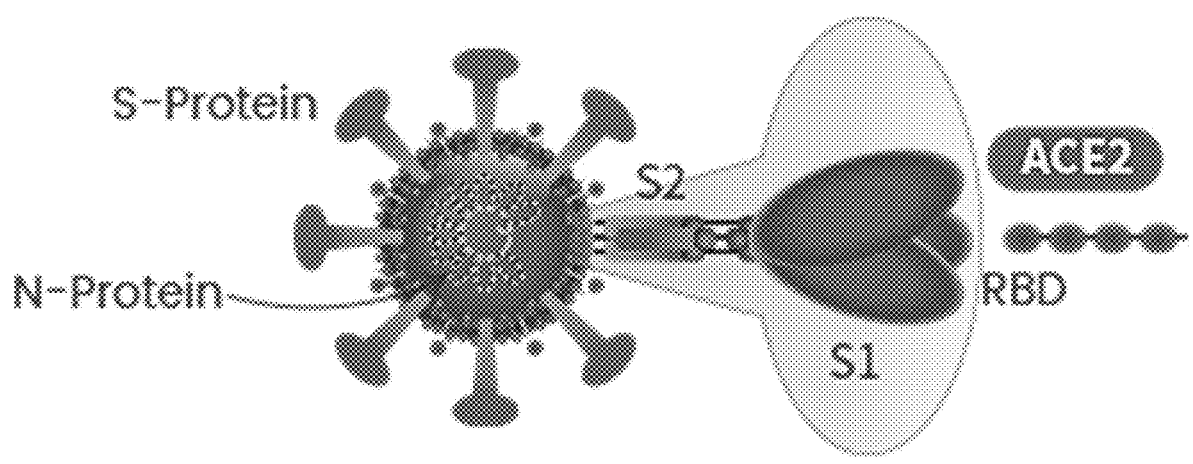
FIG. 1 is a diagram showing the spike protein of the SARS-CoV-2 (Covid-19) Spike and the S1 receptor binding domain (RBD) (S1RBD) thereof.
Figure 2:
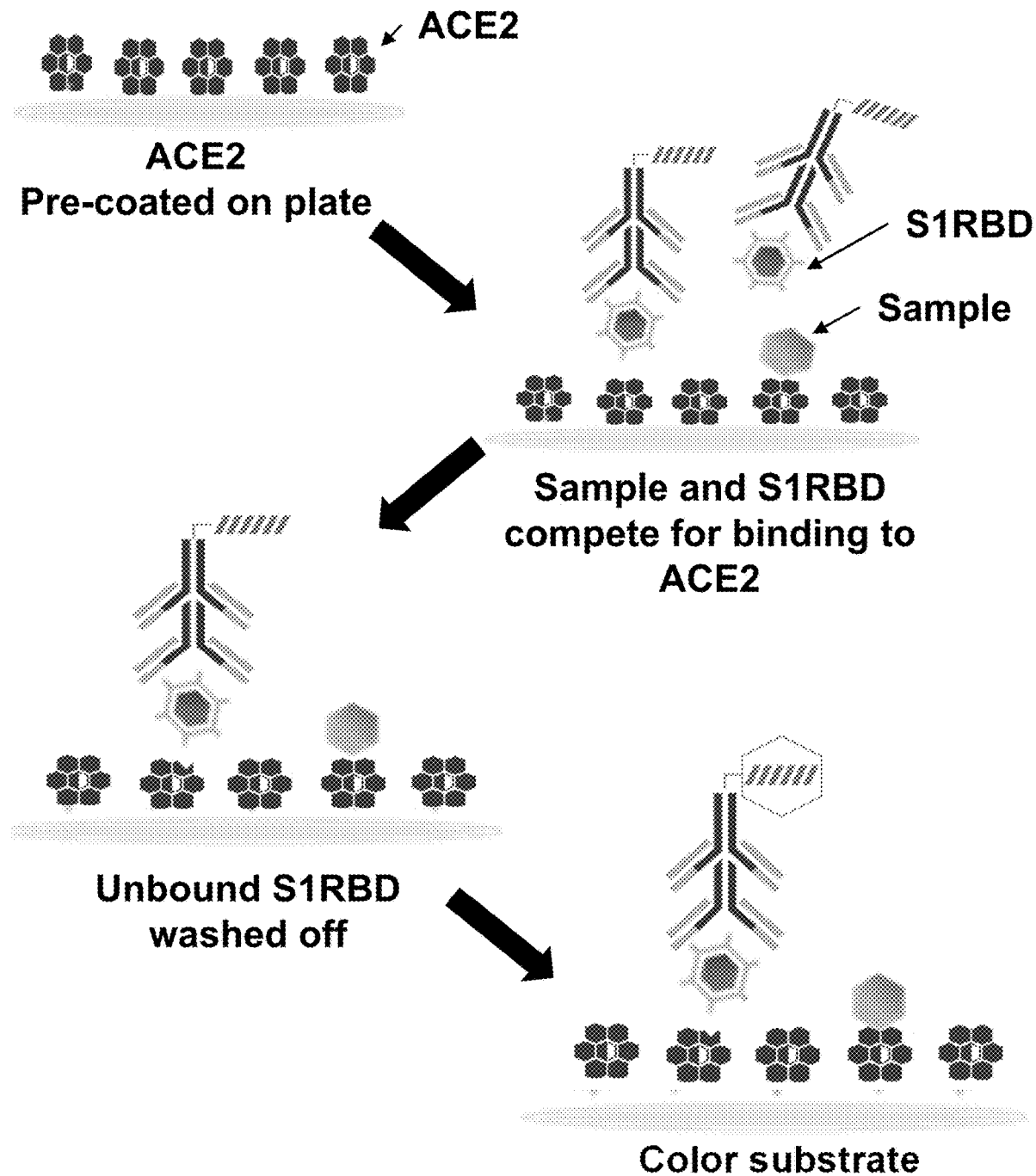
FIG. 2 schematically shows an embodiment of the assay method of the disclosure wherein Angiotensin Converting Enzyme 2 (ACE2) coats the surfaces of the wells of a microtiter plate, a mammalian cell-expressed S1RBD polypeptide tagged with an immunoglobulin Fc region tag binds to the ACE2, and detected with an anti-Fc antibody conjugated to a detectable label and which binds to the tag of the bound S1RBD polypeptide.
Figure 3:
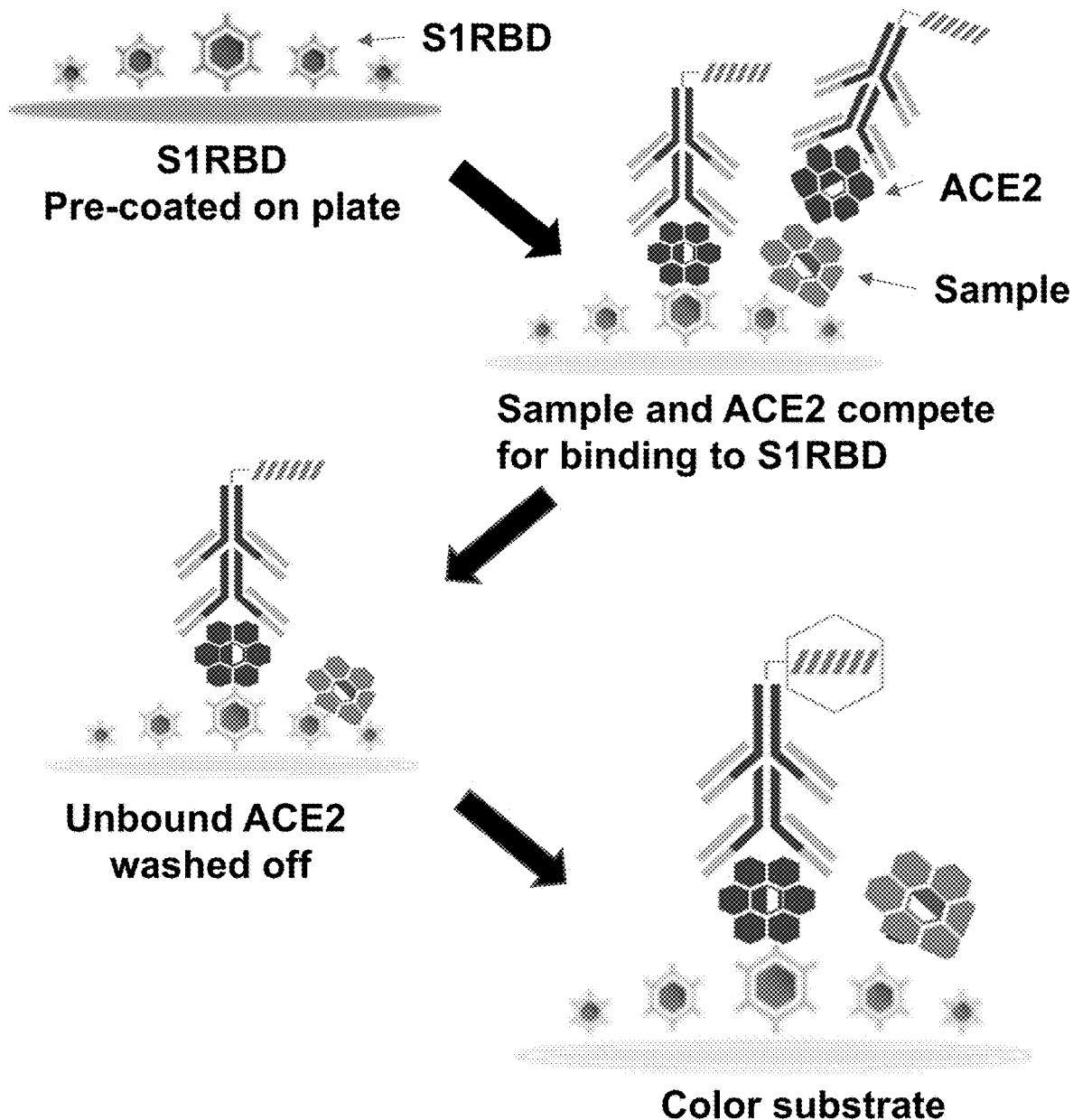
FIG. 3 schematically shows an embodiment of the assay method of the disclosure wherein mammalian cell-expressed S1RBD polypeptide coats the surfaces of the wells of a microtiter plate, Angiotensin Converting Enzyme 2 (ACE2) binds to the mammalian cell-expressed S1RBD, an anti-ACE2 antibody is bound to the ACE2 and detected with an anti-Fc antibody conjugated to a detectable label.
Figure 4:
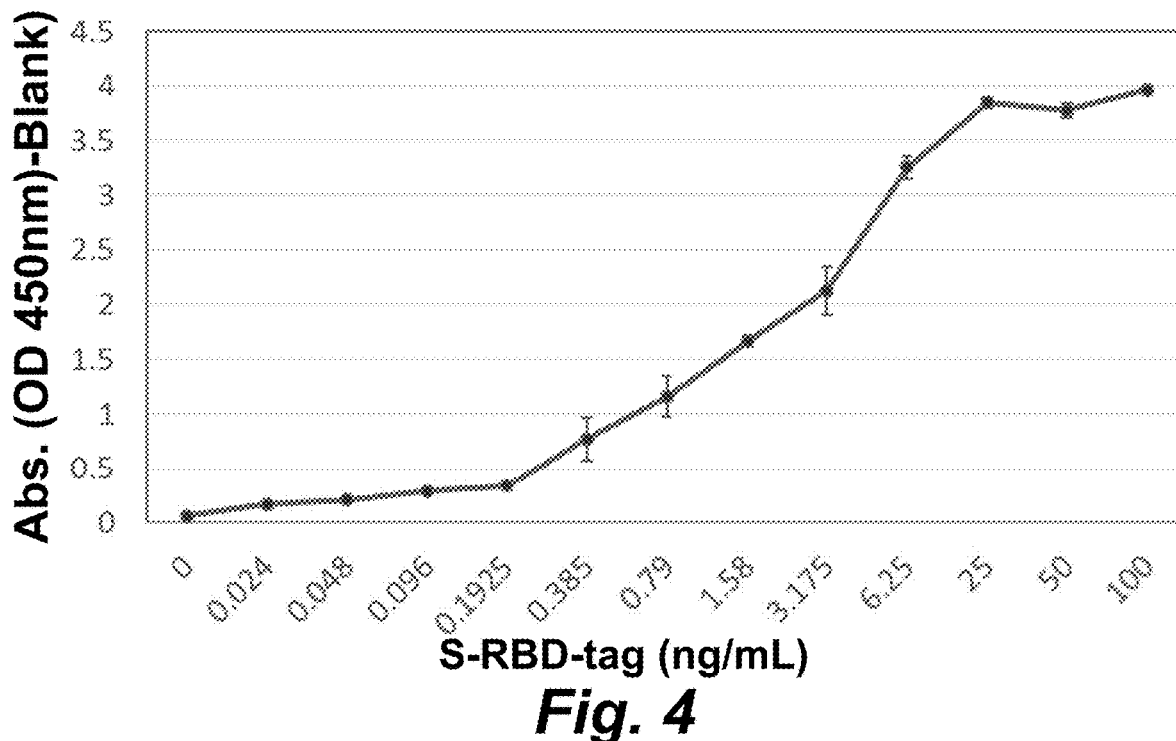
FIG. 4 shows the curve for binding of ACE2 to increasing amounts of glycosylated S1RBD polypeptide using the method of the disclosure.
Figure 5:
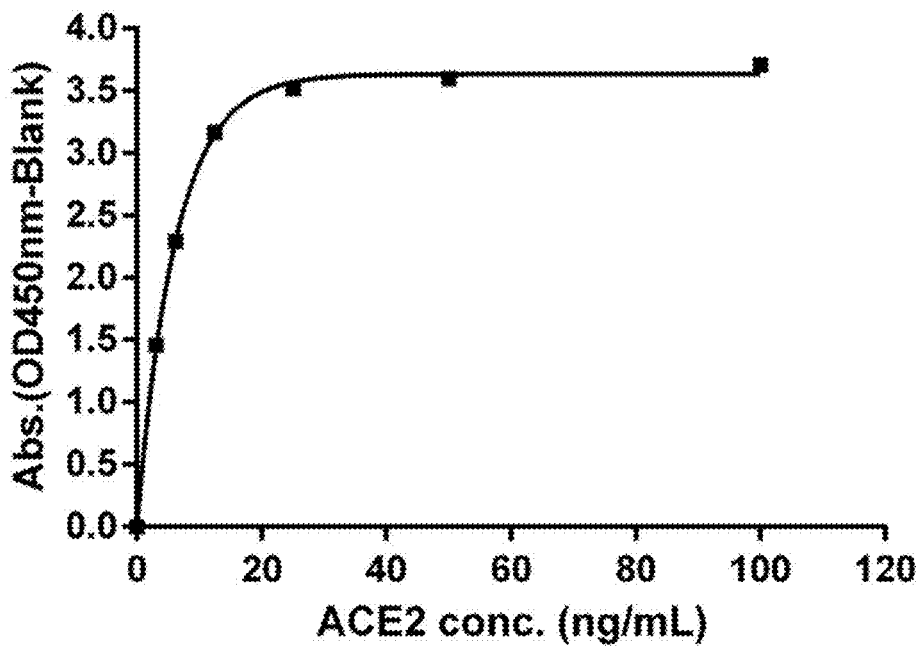
FIG. 5 shows the curve for binding of S1RBD-tag polypeptide to increasing amounts of ACE2 using the method of the disclosure.

The present disclosure encompasses embodiments of a variant ELISA-based assay that employs a glycosylated polypeptide fragment derived from the receptor binding domain (S1RBD) of the SARS-CoV-2 (Covid-19) virus spike protein and that has affinity for the extracellular domain of Angiotensin Converting Enzyme 2 (ACE2). The assays of the disclosure employ the ability of such a fragment to bind to the mammalian cell surface receptor Angiotensin Converting Enzyme 2 (ACE2) used by the SARS-CoV-2 (Covid-19) virus as a means for entry into a human cell. Accordingly, the assays of the disclosure are in two forms, as shown in FIGS. 2 and 3, one where the spike-derived polypeptide is immobilized on a surface, such as the bottom surface of a well of a microplate known in the art, and is then contacted by a buffered solution of a polypeptide derived from a mammalian ACE2 protein. In the alternative, it is the ACE2-derived polypeptide that is immobilized and contacted with the S1 RBD spike polypeptide fragment.

A notable feature of the S protein of SARS-CoV-2 is that it is extensively decorated with up to a hundred N-linked glycans, a process that occurs by viral hijacking of the host's glycosylation pathways. Glycosylation of viral structures such as S proteins, contributes to the viruses host immune evasion strategies through the masking antigenic epitopes. Structural data along with glycoproteomics analyses have proposed that extensive glycosylation of the spike protein shields against neutralizing antibodies access (Xiong et al., (2018) J. Virol. 92(4): 1-16). Importantly, the glycans on S protein possibly have an unappreciated role in both the stability of S and resultant host cell receptor interactions and cell membrane fusion during entry into the host cell. This gap in the knowledge underscores an exigent need for characterizing the relative influence of SARS-CoV-2 S protein glycosylation in identifying the molecular basis of tis interaction with ACE2, and the influence of glycans on infectivity.

It has now been found that N-glycosylation of SARS-CoV-2 is necessary for in vitro binding to ACE2 and for the entry of pseudovirus into cells. The glycosylated residues Asn343 and Asn331 on S1 RBD play a key role in its binding to ACE2 as well as infectivity. Together, these data support the conclusion that N-glycosylation of Asn343 and Asn331 is crucial for the S-ACE2 interaction and infectivity. These data allowed for the development of the assays of the disclosure.

Unlike with other ELISA-based assays known in the art, the spike S1RBD polypeptide is generated by expression of an encoding nucleic acid by a human cell expression system. This results in glycosylation of the expressed spike receptor binding domain (S1RBD) protein at least at the N343 N-glycosylation site thereof, as shown in FIGS. 8 and 9, which surprisingly and significantly increases the affinity of the S1RBD for ACE2. Use of the glycosylated form of the S1RBD, therefore, provides a significant increase in the sensitivity of the assay compared to other known assays, increasing the ability of the assay to detect much smaller amounts or concentrations of the viral protein or its sensitivity to inhibitors then previously reported, and makes possible a more economic use of reagents. Significantly, the glycosylated S1RBD polypeptide more closely resembles the glycosylated state of intact viral particles produced from an infected cell rather than does an unglycosylated S1RBD fragment that has been prepared by deglycosylation of a mammalian cell-produced S1RBD or by a bacterial expression system used for their manufacture, as shown in the data of FIGS. 4-11.

The present disclosure encompasses embodiments of the assay where the S1RBD protein fragment, when not immobilized on the surface and, therefore, intended to bind to immobilized ACE2 polypeptide includes a tag conjugated thereto. Advantageously, this tag can be, but is not limited to, an Fc portion of an immunoglobulin, most advantageously an IgG Fc region. This Fc tag can then be targeted by an anti-tag, such as an anti-immunoglobulin G (IgG) Fc-specific antibody) that has a detectable label attached thereto.

In one embodiment of the assay of the disclosure, the wells of a microtiter plate are coated with a polypeptide derived from a mammalian, and most advantageously a human, ACE2 protein. An engineered recombinant mammalian cell-expressed S1RBD-derived polypeptide is then added to the coated wells and then incubated for a time sufficient to allow binding of the S1RBD fragment to the surface immobilized ACE2 fragment.

One fragment of the SARS-CoV-2 Spike (S) protein most advantageous for use in the assays of the disclosure consists of amino acid residues R319-R514 of the S1 region of the SARS-CoV-2 spike protein. Expression of the S1RBD polypeptide from the mammalian cell expression system results in the expressed product being glycosylated. As shown in FIGS. 4-11 it has now been found that this glycosylation thereby significantly increasing the affinity of the S1RBD for the ACE2 polypeptide, or a fragment thereof.

Unbound S1RBD polypeptide is removed with washing, and a horse radish peroxidase (HRP)-conjugated anti-immunoglobulin G (IgG) antibody specific for the immunoglobulin Fc region can then be applied to the wells together with 3,3',5,5'-tetramethylbenzidine (TMB) substrate. The HRP-conjugated anti-IgG antibody will bind specifically to the S1RBD polypeptide bound to the surface-immobilized ACE2 polypeptide, react with the TMB solution, and produce a blue color, the intensity of which is proportional to the amount of bound S1RBD. The HRP-TMB reaction is halted with the addition of a Stop Solution, resulting in a blue-to-yellow color change. The intensity of the yellow color is then measured at 450 nm.

This method of the disclosure may be advantageously employed to detect, or measure the amount of, the inhibition of the interaction between S1RBD and ACE2 by a compound suspected of being an inhibitor. To detect or identify a potential inhibitor, a first assay is performed in the absence of the compound suspected of being an inhibitor. A second parallel test is performed simultaneously with the first test wherein an amount of the compound suspected of being the inhibitor is added to the second test with the S1 RBD polypeptide. A reduction in the intensity of the final yellow color of the second assay compared to the final color in the first assay indicates that the compound inhibits the S1RBD/ACE2 binding while the degree of the reduction can indicate the strength of the inhibition. Accordingly, the assays of the disclosure can be useful to identify negative effectors of the binding of S1RBD to ACE2 that may be useful in a therapeutic or prophylactic treatment for a SARS-CoV-2 (Covid-19) virus infection, or even for use against related coronavirus infections. Potential inhibitors can be, but are not limited to, small molecules (as shown in FIGS. 13 and 14) and antibodies (as shown in FIGS. 15-19), This method is also useful for the detection of the intact spike protein in a biological sample suspected of, for example, containing intact SARS-CoV-2 (Covid-19) virus or the surface antigens thereof. Compared to available means of detecting the Covid-19 spike protein in subjects suspected of being infected with the virus, the assays of the present disclosure are more significantly more sensitive.

In second embodiment of the assay of the disclosure, the wells of a microtiter plate are coated with mammalian cell-expressed S1 RBD polypeptide. A fragment of a mammalian ACE2 protein (most advantageously a human ACE2-derived polypeptide) is then added to the wells. Unbound ACE2 polypeptide is removed with washing, and an anti-ACE2-specific IgG antibody is then applied to the wells. A horse radish peroxidase-labeled (for example) anti-IgG antibody is the added to the wells in the presence of 3,3',5,5'-tetramethylbenzidine (TMB) substrate. The anti-ACE2 antibody first binds to the ACE polypeptide bound to the surface-immobilized S1RBD and then binds the labeled anti-IgG antibody to react with the TMB solution, producing a blue color that is proportional to the amount of bound ACE2. The HRP-TMB reaction is halted with the addition of the Stop Solution, resulting in a blue-to-yellow color change. The intensity of the yellow color is then measured at 450 nm.

In some embodiments, the ACE2-derived polypeptide can have a tag attached thereto, such as an immunoglobulin Fc tag. In the methods of such an embodiment, the labeled secondary antibody can be an anti-tag antibody specifically binding to the tag of the ACE2 bound to the immobile S1RBD.

The methods of the disclosure may also be readily adapted for use in lateral flow tests to provide a rapid method to detect an antiviral antibody or spike antigen in a sample such as a blood sample, nasal or sinus mucus, and the like. Such tests are less invasive, cheaper, and offer significantly more rapid results than is provided by the "gold-standard" PCR test (detecting whole virus presence). Most preferably, the lateral flow device has immobilized ACE2 polypeptide ad the flow then encounters the S1RBD-tag and HRP-anti-tag antibody.

The second variant of the method of the disclosure may also be advantageously employed to detect, or measure the amount of, the inhibition of the interaction between S1RBD and ACE2 by a compound suspected of being an inhibitor. In this case a first assay is performed in the absence of the compound suspected of being an inhibitor. A second test is performed simultaneously with the first test wherein an amount of the compound suspected of being the inhibitor is added to the second test with the ACE2 polypeptide. A reduction in the intensity of the final yellow color indicates that the compound is an inhibitor of the S1RBD/ACE2 binding and the degree of the reduction can indicate the magnitude of the inhibition.

The orientations of the two interacting components of the assay system of the disclosure can equally be used to detect inhibitors of the S1RBD/ACE2 interaction. However, the orientation where the ACE2 polypeptide is immobilized to the surface may also be used for the detection of virus or free spike protein in a sample added to the well with the S1RBD reagent as well as useful for the detection of inhibitors of S1RBD/ACE2 complexing. This embodiment provides a rapid sensitive and selective assay for the detection of intact SARS-CoV-2 (Covid-19) virus particles in a biological sample from a subject suspected of having an infection of the SARS-CoV-2 (Covid-19) virus.

The COVID-19 Spike-ACE2 binding assay kit of the disclosure provides materials and instructions for the rapid, simple, and sensitive method of the disclosure to characterize the binding affinity of the S1RBD-ACE2 complex in the presence of potential inhibitors. The in vitro enzyme-linked immunosorbent assay can measure numerous reagents and conditions simultaneously. For example, this kit can be used for screening inhibitor activity and drugs, vaccine development, and testing potential therapeutic antibodies.

One aspect of the disclosure, therefore, encompasses embodiments of a method of detecting binding between the spike-receptor binding domain (S1RBD) of the SARS-CoV-2 (Covid-19) virus and angiotensin-converting enzyme 2 (ACE2), the method comprising the steps: (a) contacting a glycosylated polypeptide derived from a spike-receptor binding domain (S1RBD) of the SARS-CoV-2 (Covid-19) virus spike (S) protein with a polypeptide derived from a mammalian ACE2, wherein the S1RBD polypeptide or the ACE2-derived polypeptide is bound to the surfaces of wells of a microtiter plate, wherein the S1RBD polypeptide is a recombinant glycosylated polypeptide expressed from a mammalian cell expression system; (b) washing the wells of unbound polypeptides; (c) either: (i) when the surface bound polypeptide is the ACE2 polypeptide, contacting the surface bound ACE2 polypeptide with the glycosylated S1RBD polypeptide, wherein the S1RBD polypeptide further comprises a tag conjugated thereto; or, (ii) when the surface bound polypeptide is the glycosylated S1RBD polypeptide, contacting the surface bound polypeptide with the ACE2 polypeptide, and then incubating the wells for a period that allows the polypeptide bound to the well surfaces to form a complex with to the polypeptide delivered thereto; (d) washing the wells of unbound polypeptides; (e) delivering to the wells from step (c)(i) a detectably labeled anti-tag-specific antibody or delivering to the wells from step (c)(ii) a detectably labeled anti-ACE2-specific antibody; (f) incubating the wells for a period to allow the antibody delivered thereto to bind to the complex formed in either step (c)(i) or (c)(ii); and (g) detecting the label on an antibody bound to the complex immobilized on the microtiter plate, thereby detecting binding of the S1RBD to the ACE2.

In some embodiments of this aspect of the invention, the polypeptide bound to wells of a microtiter plate can be an ACE2 polypeptide and is complexed in step (c)(i) to S1RBD-tag polypeptide delivered to the wells. This method can further comprise the steps: (g) repeating the assay steps (a)-(f) in the presence of a biological sample suspected of comprising SARS-CoV-2 (Covid-19) virus, wherein in step (a) the sample is added to the wells of the microtiter plate; and (h) measuring the difference between the signal from the detectable label in the absence and presence of the sample suspected of comprising SARS-CoV-2 (Covid-19) virus, wherein a reduction in the intensity of the signal generated in the presence of the compound indicates that the sample comprises SARS-CoV-2 (Covid-19) virus.

In some embodiments of this aspect of the invention the polypeptide bound to wells of a microtiter plate is a glycosylated S1RBD polypeptide expressed from a mammalian cell expression system and is complexed in step (c)(ii) to the ACE2 polypeptide delivered to the wells.

In some embodiments of this aspect of the invention the tag conjugated to the S1RBD polypeptide can be an immunoglobulin G (IgG) Fc region and the anti-tag-specific antibody can be an anti-IgG Fc-specific antibody.

In some embodiments of this aspect of the invention the S1RBD polypeptide can comprise the amino acid sequence SEQ ID NO: 1.

In some embodiments of this aspect of the invention the S1RBD polypeptide can comprise the amino acid sequence SEQ ID NO: 1 and is glycosylated at least at the N343 N-glycosylation site thereof.

In some embodiments of this aspect of the invention the label can be horse radish peroxidase (HRP).

In some embodiments of this aspect of the invention the method can further comprise the steps: (g) repeating the assay steps (a)-(f) in the presence of a compound suspected of being an inhibitor of the binding of the S1RBD polypeptide to the ACE2 polypeptide or a biological sample suspected of containing SARS-CoV-2 (Covid-19) virus or an antibody thereto, wherein in steps (c)(i) and (c)(ii) the compound is added to the wells of the microtiter plate; and (h) measuring the difference between a signal from the detectable label in the absence and presence of the compound suspected of being an inhibitor of the binding of the S1RBD polypeptide to the ACE2 polypeptide, wherein a reduction in the intensity of the signal generated in the presence of the compound indicates that the compound is an inhibitor of the S1RBD/ACE2 binding and the degree of the reduction can indicate the magnitude of the inhibition.

In some embodiments of this aspect of the invention the compound suspected of being an inhibitor of the binding of the S1RBD polypeptide to the ACE2 polypeptide can be a small molecule, an antibody, or a peptide.

In some embodiments of this aspect of the invention, the antibody can be a monoclonal antibody or in a biological sample isolated from a patient suspected of having generated anti-SARS-CoV-2 (Covid-19) virus antibodies.

Another aspect of the disclosure encompasses embodiments of a kit comprising; at least one microtiter plate comprising a plurality of wells, wherein said wells are coated with an Angiotensin Converting Enzyme 2 (ACE2) extracellular domain-derived polypeptide; a plurality of vessels, wherein said vessels can contain a wash buffer, an assay diluent, a purified glycosylated SARS-CoV-2 (Covid-19) spike protein RBD region (S1RBD)-derived polypeptide, wherein the S1RBD polypeptide is obtained by expression from a mammalian cell, and wherein the S1RBD protein has an immunoglobulin Fc tag conjugated thereto; a horse radish peroxidase-conjugated anti-immunoglobulin G (IgG) Fc-region antibody, a TMB One-Step Substrate Reagent comprising 3,3',5,5'-tetramethylbenzidine (TMB) in a buffer; and a reaction stop solution comprising about 0.2M sulfuric acid; and instructions for the use of the kit to assay the binding of the glycosylated S1RBD polypeptide to a domain of ACE2 in the absence and presence of a compound or a biological sample suspected of inhibiting said binding.

In some embodiments of the kit of the disclosure, the kit can comprise at least one microtiter plate comprising a plurality of wells, wherein said wells are coated with a glycosylated SARS-CoV-2 (Covid-19) spike protein RBD region (S1RBD)-derived polypeptide, wherein the S1RBD polypeptide is obtained by expression from a mammalian cell, a plurality of vessels, wherein said vessels can contain a wash buffer, an assay diluent, a purified extracellular domain of a recombinant ACE2 polypeptide, a horse radish peroxidase-conjugated anti-ACE2 antibody, a TMB One-Step Substrate Reagent comprising 3,3',5,5'-tetramethylbenzidine (TMB) in a buffer, and a reaction stop solution comprising about 0.2M sulfuric acid; and instruction for the use of the kit to assay the binding of the glycosylated S1RBD polypeptide to a domain of ACE2 in the absence and presence of a compound or biological sample suspected of inhibiting said binding.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLES

Example 1

Kit Material Provided

ACE2 Microplate (Item A): 96 wells (12 strips×8 wells) coated with recombinant ACE2 extracellular domain.

Wash Buffer Concentrate (20×: Potassium Chloride, 0.4%; Sodium Chloride, 16%; Potassium Dihydrogen Phosphate; 0.4%, Disodium Phosphate; Tween 20, 1.0%) (Item B): 25 ml of 20× concentrated solution.

Assay Diluent (Item E2): 15 ml of 5× concentrated buffer (5× Phosphate Buffered Saline (PBS); 7.5 wt % Bovine Serum Albumin (BSA); 0.15% 5-Bromo-5-nitro-1,3-dioxane (BND); 1.25% Tween-20) for diluting testing reagent, S1RBD-tag protein (Item F), detection antibody (Item C) and HRP-conjugated anti-Fc region antibody concentrate (Item D).

S1RBD-tag protein (Item F): 2 vials of purified human recombinant glycosylated S1RBD-tag protein (1 vial is enough to assay half microplate)

HRP-conjugated anti-Fc region antibody (Item D-2), 25 µl of 1000× concentrated HRP-conjugated anti-goat IgG.

TMB One-Step Substrate Reagent (Item H): 12 ml of 3,3',5,5'-tetramethylbenzidine (TMB) in buffered solution.

Stop Solution (Item I): 8 ml of 0.2 M sulfuric acid.

Storage

Upon receipt, the kit should be stored at −20° C. or below and used within 6 months from the date of shipment. After initial use, Wash Buffer Concentrate (Item B), Assay Diluent (Item E2), TMB One-Step Substrate Reagent (Item H), Stop Solution (Item I) should be stored at 4° C. to avoid repeated freeze-thaw cycles. Return unused wells to the pouch containing a desiccant pack, reseal along entire edge and store at −20° C. Item F should be stored at −80° C. Item C and Item D store at 2-8° C. for up to one month (store at −20° C. for up to 6 months, avoid repeated freeze-thaw cycles).

Additional Materials Required

Microplate reader capable of measuring absorbance at 450 nm.

Shaker.

Precision pipettes to deliver 2 □l to 1 ml volumes.

Adjustable 1-25 ml pipettes for reagent preparation.

100 ml and 1 liter graduated cylinders.

Distilled or deionized water.

Tubes to prepare sample dilutions.

Example 2

Sample Preparation

Mix testing reagent (e.g., potential inhibitor such as, but not limited to, a small molecule or an antibody) with S1RBD-tag protein concentrate (see Part VI, 4), then dilute the mixture with 1× Assay Diluent diluted to make a 1×S1RBD-tag protein working concentration. Each sample should contain the same 1×S1RBD-tag protein concentration.

All samples be run in at least duplicate. For the initial experiment, a serial dilution (e.g., 5-fold to 5000-fold) can be performed to determine the optimal amount of test reagent to use.

Example: To test compound A's ability to inhibit S1RBD-tag protein-ACE2 binding, dilute the 100 mM stock solution to create a dilution series of 20 mM, 2 mM, 0.2 mM, 0.02 mM, 0.002 mM and 0 mM in six separate tubes.

Pipette 225 µl of 1×S1RBD-tag protein working solution into each tube, except the 20 mM (leave this one empty). Pipette 50 µl of compound A stock, 2.5 µl of S1RBD-tag protein concentrate and 197.5ul 1× Assay Diluent into the tube labeled 20 mM. Mix thoroughly. Pipette 25 µl of the 20 mM compound A sample into the tube labeled 2 mM. Mix thoroughly. Repeat this step with each successive concentration. For each dilution, use 225 µl of 1× S1RBD-tag protein working solution and 25 µl of the prior concentration until the final concentration is reached. Mix each tube thoroughly before the next transfer.

Example 3

Reagent Preparation
1. Bring all reagents and samples to room temperature (18-25° C.) before use.
2. 5× Assay Diluent (Item E2) should be diluted 5-fold with deionized or distilled water before use.
3. If the Wash Concentrate (20×) (Item B) contains visible crystals, warm to room temperature and mix gently until dissolved. Dilute 20 ml of Wash Buffer Concentrate into deionized or distilled water to yield 400 ml of 1× Wash Buffer.
4, Briefly spin the S1RBD-tag protein (Item F) before use. Add 100 µl of 1× Assay Diluent into the vial to prepare an S1RBD-tag protein concentrate. Pipette up and down to mix gently (the concentrate can be stored at 4° C. for 1-2 days or at −80° C. for one month). The S1RBD-tag protein working solution should be diluted 100-fold with 1× Assay Diluent and used in sample preparation.
5. Briefly spin the HRP-conjugated anti-Fc region antibody (Item D-1) before use. HRP-conjugated anti-Fc region antibody concentrate should be diluted 1000-fold with 1× Assay Diluent.
EXAMPLE: Briefly spin the vial to collect contents to the bottom. Add 5 µl of HRP-conjugated anti-Fc region antibody concentrate into a tube with 5 mL 1× Assay Diluent, then pipette up and down to mix gently to prepare a 1000-fold diluted HRP-conjugated anti-Fc region antibody solution. Mix well.

Example 4

Assay Procedure:
1. Bring all reagents to room temperature (18-25° C.) before use.
2. Add 100 µl of each sample (S1RBD protein with or without a possible S1RBD-ACE2 binding inhibitor) into an appropriate well.
Note: It is recommended that all samples should be run in at least duplicate.
3. Cover well with plate holder and incubate for 2.5 hours at room temperature or overnight at 4° C. with shaking.
4. Discard the solution and wash 4 times with 1× Wash Solution. Wash by filling each well with 1× Wash Buffer (300 µl) using a multi-channel pipette or autowasher. Complete removal of liquid at each step is essential to good performance. After the last wash, remove any remaining 1× Wash Buffer by aspirating or decanting. Invert the plate and blot it against clean papertowels.
5. Add 100 µl of prepared 1×HRP-conjugated anti-Fc region antibody (see Reagent Preparation Step 6) to each well. Incubate for 1 hour at room temperature with shaking.
6. Discard the solution. Repeat the wash as described in Step 3.
7. Add 100 µl of TMB One-Step Substrate Reagent (Item H) to each well. Incubate for 30 minutes at room temperature in the dark with shaking.
8. Add 50 µl of Stop Solution (Item I) to each well. Read at 450 nm immediately.

Example 5

Kit Material Provided
COVID19 S-protein Microplate (Item A): 96 wells (12 strips×8 wells) coated with recombinant mammalian cell generated (glycosylated) COVID19 S-protein RBD domain.
Wash Buffer Concentrate (20×: Potassium Chloride, 0.4%; Sodium Chloride, 16%; Potassium Dihydrogen Phosphate; 0.4%, Disodium Phosphate; Tween 20, 1.0%) (Item B): 25 ml of 20× concentrated solution.
Assay Diluent (Item E2): 15 ml of 5× concentrated buffer (5× Phosphate Buffered Saline (PBS); 7.5 wt % Bovine Serum Albumin (BSA); 0.15% 5-Bromo-5-nitro-1,3-dioxane (BND); 1.25% Tween-20) for diluting testing reagent, ACE2 protein (Item F), detection antibody (Item C) and HRP-conjugated IgG concentrate (Item D).
ACE2 protein (Item F): 2 vials of purified human recombinant ACE2 protein (1 vial is enough to assay half microplate)
ACE2 Detection Antibody (Item C-1): 2 vials of goat anti-ACE2 (1 vial is enough to assay half microplate).
HRP-conjugated anti-goat IgG (Item D-1), 25 µl of 1000× concentrated HRP-conjugated anti-goat IgG.
TMB One-Step Substrate Reagent (Item H): 12 ml of 3,3',5,5'-tetramethylbenzidine (TMB) in buffered solution.
Stop Solution (Item I): 8 ml of 0.2 M sulfuric acid.
Storage
Upon receipt, the kit should be stored at −20° C. or below and used within 6 months from the date of shipment. After initial use, Wash Buffer Concentrate (Item B), Assay Diluent (Item E2), TMB One-Step Substrate Reagent (Item H), Stop Solution (Item I) should be stored at 4° C. to avoid repeated freeze-thaw cycles. Return unused wells to the pouch containing a desiccant pack, reseal along entire edge and store at −20° C. Item F should be stored at −80° C. Item C and Item D store at 2-8° C. for up to one month (store at −20° C. for up to 6 months, avoid repeated freeze-thaw cycles).
Additional Materials Required
Microplate reader capable of measuring absorbance at 450 nm.
Shaker.
Precision pipettes to deliver 2 □l to 1 ml volumes.
Adjustable 1-25 ml pipettes for reagent preparation.
100 ml and 1 liter graduated cylinders.
Distilled or deionized water.
Tubes to prepare sample dilutions.

Example 6

Sample Preparation
Mix testing reagent (e.g., potential inhibitor such as, but not limited to, a small molecule or an antibody) with ACE2 protein concentrate (see Part VI, 4), then dilute the mixture with 1× Assay Diluent dilute to make a 1×ACE2 protein working concentration. Each sample should contain the same 1×ACE2 protein concentration.
All samples be run in at least duplicate. For the initial experiment, a serial dilution (e.g., 5-fold to 5000-fold) can be performed to determine the optimal amount of test reagent to use.
Example: To test compound A's ability to inhibit Spike-ACE2 binding, dilute the 100 mM stock solution to create a dilution series of 20 mM, 2 mM, 0.2 mM, 0.02 mM, 0.002 mM and 0 mM in six separate tubes.
Pipette 225 µl of 1×ACE2 protein working solution into each tube, except the 20 mM (leave this one empty). Pipette 50 µl of compound A stock, 2.5 µl of ACE2 protein concentrate and 197.5 µl 1× Assay Diluent into the tube labeled 20 mM. Mix thoroughly. Pipette 25 µl of the 20 mM compound A sample into the tube labeled 2 mM. Mix thoroughly. Repeat this step with each successive concentration. For each dilution, use 225 µl of 1×ACE2 protein working solution and 25 µl of the prior concentration until the final concentration is reached. Mix each tube thoroughly before the next transfer.

Example 7

Reagent Preparation

1. Bring all reagents and samples to room temperature (18-25° C.) before use.

2. 5× Assay Diluent (Item E2) should be diluted 5-fold with deionized or distilled water before use.

3. If the Wash Concentrate (20×) (Item B) contains visible crystals, warm to room temperature and mix gently until dissolved. Dilute 20 ml of Wash Buffer Concentrate into deionized or distilled water to yield 400 ml of 1× Wash Buffer.

4. Briefly spin the ACE2 protein (Item F) before use. Add 100 µl of 1× Assay Diluent into the vial to prepare an ACE2 protein concentrate. Pipette up and down to mix gently (the concentrate can be stored at 4° C. for 1-2 days or at −80° C. for one month). The ACE2 protein working solution should be diluted 100-fold with 1× Assay Diluent and used in sample preparation.

5. Briefly spin the detection antibody (Item C-1) before use. Add 100 µl of 1× Assay Diluent into the vial to prepare a detection antibody concentrate. Pipette up and down to mix gently (the concentrate can be stored at 4° C. for 5 days or at −80° C. for one month). The goat anti-ACE2 antibody concentrate should be diluted 55-fold with 1× Assay Diluent and used in step 4 of the assay procedure.

6. Briefly spin the HRP-conjugated anti-goat IgG (Item D-1) before use. HRP-conjugated anti-goat IgG concentrate should be diluted 1000-fold with 1× Assay Diluent. EXAMPLE: Briefly spin the vial to collect contents to the bottom. Add 5 µl of HRP-conjugated anti-goat IgG concentrate into a tube with 5 mL 1× Assay Diluent, then pipette up and down to mix gently to prepare a 1000-fold diluted HRP-conjugated anti-goat IgG solution. Mix well.

Example 8

Assay Procedure:

1. Bring all reagents to room temperature (18-25° C.) before use.

2. Add 100 µl of each sample into an appropriate well.
Note: It is recommended that all samples should be run in at least duplicate.

3. Cover well with plate holder and incubate for 2.5 hours at room temperature or overnight at 4° C. with shaking.

4. Discard the solution and wash 4 times with 1× Wash Solution. Wash by filling each well with 1× Wash Buffer (300 µl) using a multi-channel pipette or autowasher. Complete removal of liquid at each step is essential to good performance. After the last wash, remove any remaining 1× Wash Buffer by aspirating or decanting. Invert the plate and blot it against clean papertowels.

5. Add 100 µl of prepared 1× Detection Antibody (Reagent Preparation step 5) to each well. Incubate for 1 hour at room temperature with shaking.
Discard the solution. Repeat the wash as described in Step 3.

6. Add 100 µl of prepared 1×HRP-conjugated anti-goat IgG (see Reagent Preparation Step 6) to each well. Incubate for 1 hour at room temperature with shaking.

7. Discard the solution. Repeat the wash as described in Step 3.

8. Add 100 µl of TMB One-Step Substrate Reagent (Item H) to each well. Incubate for 30 minutes at room temperature in the dark with shaking.

9. Add 50 µl of Stop Solution (Item I) to each well. Read at 450 nm immediately.

Example 9

In vitro binding of viral components to human ACE2: A high throughput screening method to measure molecular binding between the SARS-CoV-2 S protein and the human ACE2 protein. Microtiter plates were coated with either recombinant SARS-CoV-2 S protein S1 domain, S2 domain, or nucleocapsid (N) protein. Systematic incubation of these plates with recombinant human ACE2 confirmed that ACE2 specifically bound to S1RBD and not to any of the other viral components tested (FIG. 10A). Furthermore, recombinant SARS-CoV-2 S1RBD generated by expression within human HEK293T cultured cells bound to the ACE2 with significantly stronger affinity compared to recombinant S1 RBD generated by expression within *E. coli* (FIG. 10B). These data indicate that eukaryotic-specific post-translational modifications influences ACE2/S1RBD binding affinity.

Example 10

Figure 6:
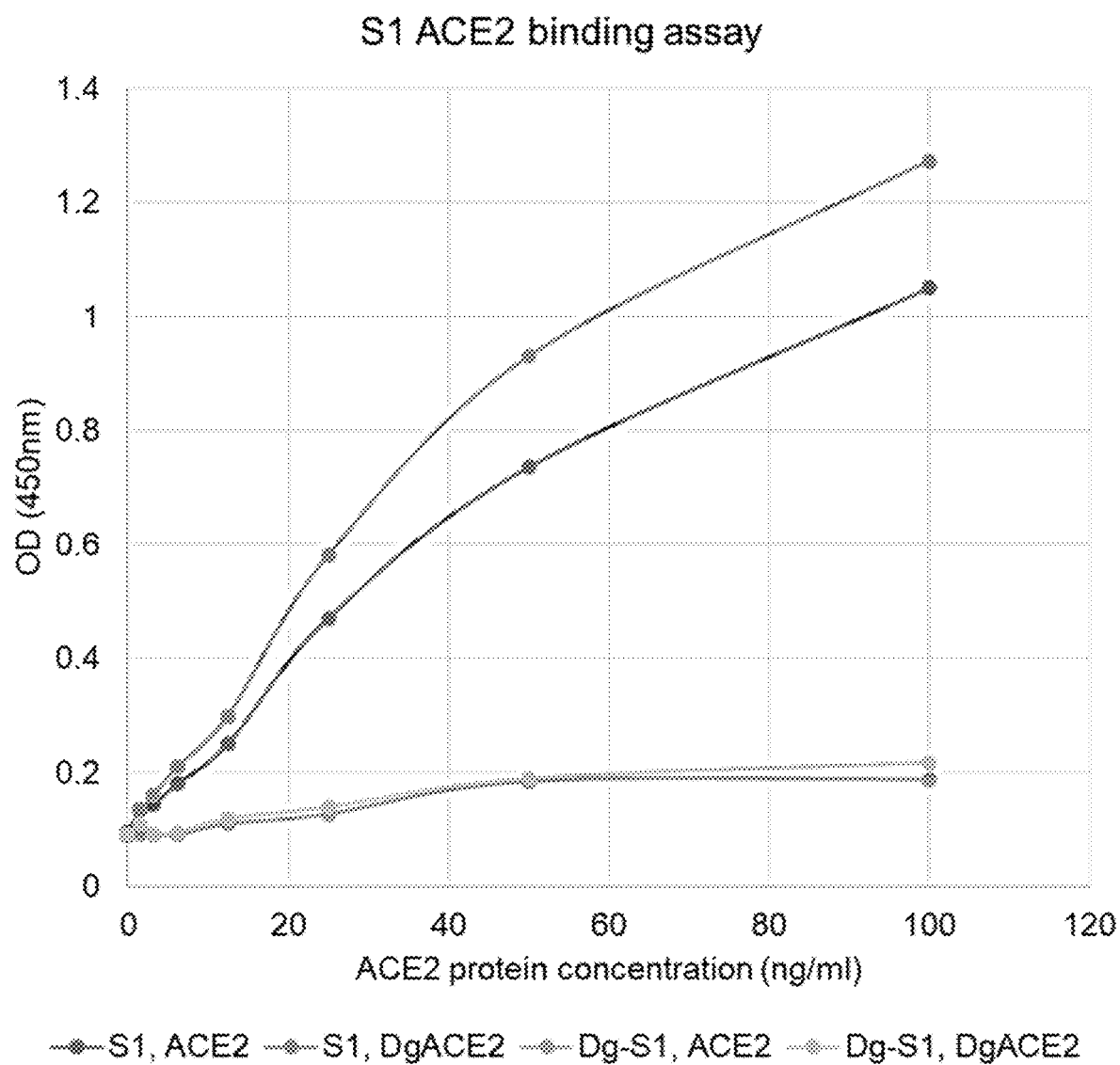
FIG. 6 shows that S1RBD protein glycosylation is essential for binding to ACE2. The S-ACE2 interaction was assessed using untreated and deglycosylated SARS-CoV-2 S1RBD and untreated and deglycosylated human ACE2 with the binding assay. Untreated and deglycosylated S1 RBD proteins were coated on a 96-well plate respectively. A series of concentrations (0, 20, 40, 60, 80, 100 ng/ml) of untreated or deglycosylated ACE2 protein were added into the wells and bound ACE2 protein was detected using anti-ACE2 antibody and HRP conjugated secondary antibody. With untreated S1RBD protein, increasing bound ACE2 protein, treated or deglycosylated, was detected with increasing ACE2 protein concentrations. With deglycosylated S1RBD protein, no increase in bound ACE2 protein, treated or deglycosylated, was detected with an increase ACE2 protein concentration
Figure 7:
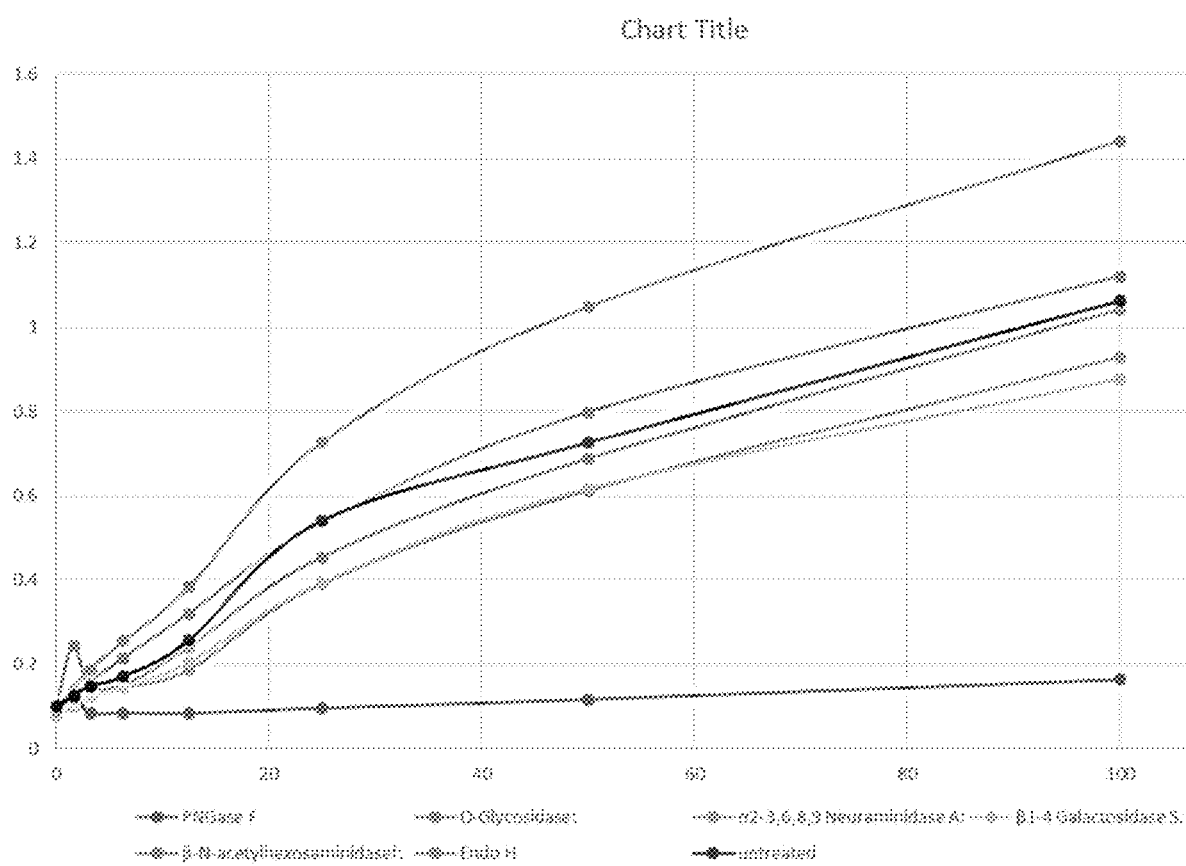
FIG. 7 shows that N-linked S1RBD protein glycosylation is essential for binding to ACE2. The S-ACE2 interaction was assessed using untreated and deglycosylated SARS-CoV-2 S1RBD with different deglycosylases. S1RBD protein was treated using different deglycosylases: PNGase F, O-glycosidase, α2-3,6,8,9 neuraminidase A, β1-4 galactosidase S, β-N-acetylhexosaminidase$_f$, and Endo H.

N-linked glycosylation of S1 RBD protein is required for binding to ACE2: To determine the extent to which glycosylation influences ACE2/S1RBD binding affinity, S1RBD generated within HEK293T cultured cells was deglycosylated to remove both N and O-linked glycans. Whereas untreated S1RBD bound to ACE2 in a dose-dependent manner, deglycosylation of S1 RBD abolished its binding to ACE2 (FIG. 6). Importantly, deglycosylation of ACE2 had a minimal effect on binding (FIG. 6). To further interrogate which glycan linkages function in ACE2/S1 RBD binding, S1RBD was treated with deglycosylation enzymes that specifically target different glycosylation links. Of the enzymes tested, only treatment with PNGase, which cleaves N-linked oligosaccharides, significantly lowered ACE2/S1 RBD binding affinity (FIG. 7).

Example 11

Glycosylation of S1RBD at Asn343 is essential for interaction with ACE2: The SARS-CoV-2 S protein has 22 putative glycosites as determined by the presence of the N-X-S/T, X≠P motif sequence (Zhang et al., (2020) *Mol. Cell. Proteomics*). Of these sites, N331 and N343 are located on the RBD and have been shown to be n-glycosylated (Zhang et al., (2020) *Mol. Cell. Proteomics*) and when mutated to glutamine were found to drastically reduce viral infectivity (Li et al., (2020) Cell 182: 1284-1294). To determine whether these residues function in ACE2/S1RBD molecular interaction during binding, three mutated recombinants of S1 RBD were generated: N343Q, N331Q, and a N343Q/N331Q double mutation. Measurement of in vitro binding activity of these mutants to ACE2 revealed that binding was abolished in both N343Q and N331Q/N343Q and was significantly lower in the N331Q mutant version of S1 RBD (FIG. 7).

Example 12

Mutation of glycosylation sites significantly reduces pseudoviral infectivity: To measure the influence of the N343 and N331 glycosites on infectivity, a pseudovirus system was used that expresses the SARS-CoV-2 S1 RBD on a viral particle surface, while a plasmid encoding for luciferase is contained inside the particle. When applied to cultured mammalian cells, the S protein binds the ACE2 receptor, the membranes of the viral particle and host cell fuse, releasing the plasmid into the cell where luciferase is expressed. In addition to the wild type version of the S1RBD, pseudovirus was generated that expressed on the viral surface mutated versions of S1RBD, namely N343Q, N331Q, and a N343Q/N331Q double mutation. Measurement of luciferase activity within infected cells showed that the double glycosylation deletions at N331 and N343 resulted in a substantial reduction in viral infectivity (>80% inhibition), whereas single deletion at N331Q caused modest with the infectivity of N331Q (reduced by less than 20%) and N343Q by about 50% (FIG. 8).

These data demonstrate that double glycosylation mutations in S1RBD (N331Q and N343Q) significantly reduced infectivity, suggesting that the two glycosylation sites in the RBD region may participate in the binding of the receptor or maintain the conformation of the RBD region. Expression of wild type spike and three Spike mutants was confirmed in the VSV-Spike viral particles.

Example 13

Monoclonal anti-SARS-COV-2 S1RBD antibody inhibits SARS-COV-2-S-driven entry: It was tested whether antibodies against the RBD could block SARS-2-S driven entry. Mouse anti-S1RBD monoclonal antibodies were screened for the neutralization activity using the pseudoviral neutralization test (PVNT) assay.

As shown in FIG. 9, monoclonal antibodies 807, 814, 844, and 845 inhibited more than 50% of SARS-COV-2-S-driven entry at 2 µg/ml. MM57, a commercial neutralizing antibody (Sinobio) served as a positive control.

Example 14

COVID-19 patient sera exhibit a high level of neutralization activity (blockade of SARS-COV-2-S driven entry): To determine the applicability of the neutralization test for measuring neutralizing activity of COVID-19 patient sera, 15 sera obtained from convalescent COVID-19 patients were collected and tested using the PVNT assay. The results indicated that all of them inhibited SARS-COV-2-S-, but not VSV-G-, driven entry in a concentration-dependent manner (FIG. 19). No inhibition was observed when the serum from health person used as a normal control (FIG. 19).

Example 15

Zafirlukast, a small molecule, neutralizes SARS-COV-2 Spike-driven entry: Small molecule inhibitors were tested using the PVNT. Zafirlukast, a small molecule inhibited SARS-COV-2-S- but not VSV-G-driven entry in a concentration-dependent manner (FIG. 13). No inhibition was observed when cefoperazone and camostat or DMSO (FIG. 13). A Western blot analysis confirmed the expression of spike protein (approximately 165 kDa band) in the VSV-spike pseudoviral particles probed with a mouse anti SARS-COV-2 S1RBD monoclonal antibody (130-10864). No signal was detected in the VSV-G pseudoviral particles.

What is claimed:

1. A method of detecting an antibody inhibiting binding between the spike-receptor binding domain (S1RBD) of the SARS-CoV-2 (Covid-19) virus and angiotensin-converting enzyme 2 (ACE2), the method comprising the steps:
   (a) contacting a glycosylated fragment of the spike-receptor binding domain (S1RBD) of the SARS-CoV-2 (Covid-19) virus spike (S) protein with a polypeptide fragment from a mammalian ACE2 protein, wherein the S1RBD polypeptide fragment is bound to the wells of a microtiter plate, is a recombinant glycosylated polypeptide expressed from a mammalian cell expression system, and has the amino acid sequence SEQ ID NO: 1, and the ACE2 fragment has the amino acid sequence SEQ ID NO: 2;
   (b) contacting the well-bound glycosylated S1RBD fragment with the ACE2 fragment, and then incubating the wells for a period that allows the well-bound glycosylated S1RBD fragment to form a well-bound complex with the ACE2 fragment delivered thereto;
   (c) washing the wells of unbound polypeptides;
   (d) delivering to the wells from step (c) a detectably labeled anti-ACE2-specific antibody;
   (e) incubating the wells for a period to allow the anti-ACE2-specific antibody to bind to the well-bound complex formed in step (b); and
   (f) washing the wells of unbound polypeptides;
   (g) detecting a signal generated by the label on the anti-ACE2-specific antibody bound to the well-bound complex, thereby detecting binding of the S1RBD fragment to the ACE2 fragment;
   (h) repeating steps (a)-(g), wherein in step (a) a suspected antibody inhibitor of S1RBD/ACE2 binding is added to the wells of the microtiter plate, wherein the suspected antibody inhibitor is either (i) an isolated antibody or (ii) a component of a biological sample suspected of comprising a suspected antibody inhibitor of S1RBD/ACE2 binding; and
   (i) measuring the difference between the signals from the detectable label in the absence and presence of the suspected S1RBD/ACE2 binding inhibitor, wherein lower signal intensity generated in the presence of the suspected inhibitor compared to the signal intensity in the absence of the suspected inhibitor indicates that the suspected inhibitor is an inhibitor or comprises an inhibitor of S1RBD/ACE2 binding and the degree of the signal intensity reduction further indicates the magnitude of the inhibition.

2. The method of claim 1, wherein the ACE2 fragment has the amino acid sequence SEQ ID NO: 2.

3. The method of claim 1, wherein the label is horse radish peroxidase (HRP).

* * * * *

SEQUENCE LISTING

```
<160> NUMBER OF SEQ ID NOS: 2

<210> SEQ ID NO 1
<211> LENGTH: 671
<212> TYPE: PRT
<213> ORGANISM: Artificial sequence
<220> FEATURE:
<223> OTHER INFORMATION: Recombinant SARS-Co-2 (Covid-19) Receptor
      Binding Domain

<400> SEQUENCE: 1

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
```

```
                130                 135                 140
Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
                180                 185                 190

Val Phe Lys Asn Ile Asp Gly Tyr Phe Lys Ile Tyr Ser Lys His Thr
                195                 200                 205

Pro Ile Asn Leu Val Arg Asp Leu Pro Gln Gly Phe Ser Ala Leu Glu
210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
                260                 265                 270

Arg Thr Phe Leu Leu Lys Tyr Asn Glu Asn Gly Thr Ile Thr Asp Ala
                275                 280                 285

Val Asp Cys Ala Leu Asp Pro Leu Ser Glu Thr Lys Cys Thr Leu Lys
290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
                340                 345                 350

Trp Asn Arg Lys Arg Ile Ser Asn Cys Val Ala Asp Tyr Ser Val Leu
                355                 360                 365

Tyr Asn Ser Ala Ser Phe Ser Thr Phe Lys Cys Tyr Gly Val Ser Pro
                370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
                420                 425                 430

Val Ile Ala Trp Asn Ser Asn Asn Leu Asp Ser Lys Val Gly Gly Asn
                435                 440                 445

Tyr Asn Tyr Leu Tyr Arg Leu Phe Arg Lys Ser Asn Leu Lys Pro Phe
                450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
                500                 505                 510

Leu Ser Phe Glu Leu Leu His Ala Pro Ala Thr Val Cys Gly Pro Lys
                515                 520                 525

Lys Ser Thr Asn Leu Val Lys Asn Lys Cys Val Asn Phe Asn Phe Asn
                530                 535                 540

Gly Leu Thr Gly Thr Gly Val Leu Thr Glu Ser Asn Lys Lys Phe Leu
545                 550                 555                 560
```

```
Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
            610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
            645                 650                 655

Asn Asn Ser Tyr Glu Cys Asp Ile Pro Ile Gly Ala Gly Ile Cys
            660                 665                 670

<210> SEQ ID NO 2
<211> LENGTH: 723
<212> TYPE: PRT
<213> ORGANISM: Artificial sequence
<220> FEATURE:
<223> OTHER INFORMATION: Extracellular domain human Angiotensin
      Converting Enzyme 2

<400> SEQUENCE: 2

Gln Ser Thr Ile Glu Glu Gln Ala Lys Thr Phe Leu Asp Lys Phe Asn
1               5                   10                  15

His Glu Ala Glu Asp Leu Phe Tyr Gln Ser Ser Leu Ala Ser Trp Asn
            20                  25                  30

Tyr Asn Thr Asn Ile Thr Glu Glu Asn Val Gln Asn Met Asn Asn Ala
        35                  40                  45

Gly Asp Lys Trp Ser Ala Phe Leu Lys Glu Gln Ser Thr Leu Ala Gln
    50                  55                  60

Met Tyr Pro Leu Gln Glu Ile Gln Asn Leu Thr Val Lys Leu Gln Leu
65                  70                  75                  80

Gln Ala Leu Gln Gln Asn Gly Ser Ser Val Leu Ser Glu Asp Lys Ser
                85                  90                  95

Lys Arg Leu Asn Thr Ile Leu Asn Thr Met Ser Thr Ile Tyr Ser Thr
            100                 105                 110

Gly Lys Val Cys Asn Pro Asp Asn Pro Gln Glu Cys Leu Leu Leu Glu
        115                 120                 125

Pro Gly Leu Asn Glu Ile Met Ala Asn Ser Leu Asp Tyr Asn Glu Arg
    130                 135                 140

Leu Trp Ala Trp Glu Ser Trp Arg Ser Glu Val Gly Lys Gln Leu Arg
145                 150                 155                 160

Pro Leu Tyr Glu Glu Tyr Val Val Leu Lys Asn Glu Met Ala Arg Ala
                165                 170                 175

Asn His Tyr Glu Asp Tyr Gly Asp Tyr Trp Arg Gly Asp Tyr Glu Val
            180                 185                 190

Asn Gly Val Asp Gly Tyr Asp Tyr Ser Arg Gly Gln Leu Ile Glu Asp
        195                 200                 205

Val Glu His Thr Phe Glu Glu Ile Lys Pro Leu Tyr Glu His Leu His
    210                 215                 220

Ala Tyr Val Arg Ala Lys Leu Met Asn Ala Tyr Pro Ser Tyr Ile Ser
225                 230                 235                 240

Pro Ile Gly Cys Leu Pro Ala His Leu Leu Gly Asp Met Trp Gly Arg
```

```
                    245                 250                 255
Phe Trp Thr Asn Leu Tyr Ser Leu Thr Val Pro Phe Gly Gln Lys Pro
                260                 265                 270
Asn Ile Asp Val Thr Asp Ala Met Val Asp Gln Ala Trp Asp Ala Gln
            275                 280                 285
Arg Ile Phe Lys Glu Ala Glu Lys Phe Val Ser Val Gly Leu Pro
        290                 295                 300
Asn Met Thr Gln Gly Phe Trp Glu Asn Ser Met Leu Thr Asp Pro Gly
305                 310                 315                 320
Asn Val Gln Lys Ala Val Cys His Pro Thr Ala Trp Asp Leu Gly Lys
                325                 330                 335
Gly Asp Phe Arg Ile Leu Met Cys Thr Lys Val Thr Met Asp Asp Phe
                340                 345                 350
Leu Thr Ala His His Glu Met Gly His Ile Gln Tyr Asp Met Ala Tyr
                355                 360                 365
Ala Ala Gln Pro Phe Leu Leu Arg Asn Gly Ala Asn Glu Gly Phe His
            370                 375                 380
Glu Ala Val Gly Glu Ile Met Ser Leu Ser Ala Ala Thr Pro Lys His
385                 390                 395                 400
Leu Lys Ser Ile Gly Leu Leu Ser Pro Asp Phe Gln Glu Asp Asn Glu
                405                 410                 415
Thr Glu Ile Asn Phe Leu Leu Lys Gln Ala Leu Thr Ile Val Gly Thr
                420                 425                 430
Leu Pro Phe Thr Tyr Met Leu Glu Lys Trp Arg Trp Met Val Phe Lys
                435                 440                 445
Gly Glu Ile Pro Lys Asp Gln Trp Met Lys Lys Trp Trp Glu Met Lys
            450                 455                 460
Arg Glu Ile Val Gly Val Val Glu Pro Val Pro His Asp Glu Thr Tyr
465                 470                 475                 480
Cys Asp Pro Ala Ser Leu Phe His Val Ser Asn Asp Tyr Ser Phe Ile
                485                 490                 495
Arg Tyr Tyr Thr Arg Thr Leu Tyr Gln Phe Gln Phe Gln Glu Ala Leu
                500                 505                 510
Cys Gln Ala Ala Lys His Glu Gly Pro Leu His Lys Cys Asp Ile Ser
            515                 520                 525
Asn Ser Thr Glu Ala Gly Gln Lys Leu Phe Asn Met Leu Arg Leu Gly
        530                 535                 540
Lys Ser Glu Pro Trp Thr Leu Ala Leu Glu Asn Val Val Gly Ala Lys
545                 550                 555                 560
Asn Met Asn Val Arg Pro Leu Leu Asn Tyr Phe Glu Pro Leu Phe Thr
                565                 570                 575
Trp Leu Lys Asp Gln Asn Lys Asn Ser Phe Val Gly Trp Ser Thr Asp
                580                 585                 590
Trp Ser Pro Tyr Ala Asp Gln Ser Ile Lys Val Arg Ile Ser Leu Lys
            595                 600                 605
Ser Ala Leu Gly Asp Lys Ala Tyr Glu Trp Asn Asp Asn Glu Met Tyr
        610                 615                 620
Leu Phe Arg Ser Ser Val Ala Tyr Ala Met Arg Gln Tyr Phe Leu Lys
625                 630                 635                 640
Val Lys Asn Gln Met Ile Leu Phe Gly Glu Glu Asp Val Arg Val Ala
                645                 650                 655
Asn Leu Lys Pro Arg Ile Ser Phe Asn Phe Phe Val Thr Ala Pro Lys
                660                 665                 670
```

-continued

```
Asn Val Ser Asp Ile Ile Pro Arg Thr Glu Val Glu Lys Ala Ile Arg
        675                 680                 685

Met Ser Arg Ser Arg Ile Asn Asp Ala Phe Arg Leu Asn Asp Asn Ser
        690                 695                 700

Leu Glu Phe Leu Gly Ile Gln Pro Thr Leu Gly Pro Pro Asn Gln Pro
705                 710                 715                 720

Pro Val Ser
```